United States Patent
Dong et al.

(10) Patent No.: US 6,361,947 B1
(45) Date of Patent: Mar. 26, 2002

(54) COMPLEXITY MANAGEMENT AND ANALYSIS OF GENOMIC DNA

(75) Inventors: Shoulian Dong, San Jose; Robert J. Lipshutz, Palo Alto; David J. Lockhart, Del Mar, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/428,350

(22) Filed: Oct. 27, 1999

Related U.S. Application Data

(60) Provisional application No. 60/105,867, filed on Oct. 27, 1998, and provisional application No. 60/136,125, filed on May 26, 1999.

(51) Int. Cl.[7] .......................... C12Q 1/68; C07H 21/02
(52) U.S. Cl. ........................................ 435/6; 536/23.1
(58) Field of Search .............................. 435/6; 536/23.1

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,487,985 A | 1/1996 | McClelland et al. | |
| 5,512,439 A | 4/1996 | Hornes et al. | |
| 5,710,000 A | 1/1998 | Sapolsky et al. | |
| 5,712,127 A | 1/1998 | Malek et al. | |
| 5,763,239 A | 6/1998 | Short et al. | |
| 5,837,832 A | * 11/1998 | Chee et al. | |
| 5,851,770 A | 12/1998 | Babon et al. | |
| 5,858,656 A | 1/1999 | Deugau et al. | |
| 5,876,929 A | 3/1999 | Wigler et al. | |
| 6,001,574 A | 12/1999 | Short et al. | |
| 6,004,783 A | 12/1999 | Ausubel et al. | |
| 6,013,445 A | 1/2000 | Albrecht et al. | |
| 6,027,877 A | 2/2000 | Wagner et al. | |
| 6,027,945 A | 2/2000 | Smith et al. | |
| 6,033,861 A | 3/2000 | Schafer et al. | |
| 6,060,240 A | 5/2000 | Kamb et al. | |
| 6,060,245 A | 5/2000 | Sorge et al. | |

FOREIGN PATENT DOCUMENTS

| | | | |
|---|---|---|---|
| WO | WO93/22457 | * 11/1993 | |
| WO | WO99/43853 | 9/1999 | |

OTHER PUBLICATIONS

Chee et al., "Accessing Genetic Information with High–Density DNA Arrays," Science, 1996, vol. 274, pp. 610–614.*

"Fingerprinting Methods Based on Arbitrarily Primed PCR" M.R. Micheli and R. Borg Eds (1997) Springer Lab Manual, Springer–Verlag Berlin Heidelberg Pubs. see especially Chapter 7 R. Arribas et al. "Arbitrarily Primed PCR and RAPDS".

Wagner R. and Radman, M. (1995). Mismatch binding protein–based mutation detection systems. In "Methods: a Companion to Methods in Enzymology" 7, 199–203.

* cited by examiner

Primary Examiner—John S. Brusca
Assistant Examiner—Young Kim
(74) Attorney, Agent, or Firm—Affymetrix, Inc.; Wei Zhou

(57) ABSTRACT

The present invention provides for novel methods of sample preparation and analysis involving reproducibly reducing the complexity of a nucleic sample. The invention further provides for analysis of the above sample by hybridization to an array which may be specifically designed to interrogate the desired fragments for particular characteristics, such as, for example, the presence or absence of a polymorphism. The invention further provides for novel methods of using a computer system to model enzymatic reactions in order to determine experimental conditions before conducting actual experiments.

30 Claims, 16 Drawing Sheets

(A, C, G, T)-HGE250-350; ~16Mb

PCR PRIMER (A, T)-HGE250-350; ~4Mb

PCR PRIMER (T)-HGE250-350; ~1Mb

PCR PRIMER

| | Cleavage Frequency of First Enzyme | Sites in λ | Size of Captured Sequence (bp) |
|---|---|---|---|
| AlwI / HgaI | 1/512 | 58 | 5 |
| BbsI / BbvI | 1/2048 | 24 | 6 |
| BsaI / HgaI | 1/2048 | 2 | 5 |
| BseRI / BbvI | 1/2048 | 19 | 8 |
| BsmAI / HgaI | 1/512 | 37 | 5 |
| BspMI / BbvI | 1/2048 | 41 | 8 |
| Esp3I / HgaI | 1/2048 | 14 | 5 |
| EarI / HgaI | 1/2048 | 34 | 4 |
| HgaI / BsmFI | 1/512 | 102 | 10 |
| HphI / BbvI | 1/512 | 168 | 7 |
| MboII / BbvI | 1/512 | 130 | 7 |
| MnlI / HgaI | 1/128 | 262 | 6 |
| PleI / HgaI | 1/512 | 61 | 5 |
| SapI / HgaI | 1/8192 | 10 | 4 |
| SfaNI / FokI | 1/512 | 169 | 9 |

FIG. 5

| Primer | Sequence | Annealing T | Polymerase | # Present | % |
|---|---|---|---|---|---|
| Total Genome | | | | | |
| sdp5 | nncgttgg | 30 | ThermoSequenase | 434 | 6.1 |
| sdp3 | agagctgc | 30 | TaqGold | 393 | 5.6 |
| DOP | ccgactcgagnnnnnnatgtgg | 30 | TaqGold | 264 | 3.7 |
| sdp8 | nnnnnngccgttgg | 45 | TaqGold | 247 | 3.5 |
| sdp8-10 | nnnnatgccgttgg | 45 | TaqGold | 218* | 3.1* |
| sdp8 | nnnnnngccgttgg | 55 | TaqGold | 206 | 2.9 |
| | | | | 114 | 1.6 |

*Results of 20µg/200µl hybridization.

FIG. 8

COMPLEXITY MANAGEMENT AND ANALYSIS OF GENOMIC DNA

RELATED APPLICATIONS

This application claims the benefit of U.S. Provisional Application Ser. Nos. 60/105,867, filed Oct. 27, 1998, and 60/136,125, filed May 26, 1999, the entire teachings of which are incorporated herein by reference.

BACKGROUND OF THE INVENTION

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, alzheimers or alcoholism. Answers to the world's food distribution problems may be held within the exploitation of genomic information from plants and animals.

It is estimated that by the Spring of 2000 a reference sequence of the entire human genome will be sequenced allowing for types of genetic analysis that were never before possible. Novel methods of sample preparation and sample analysis are needed to provide for the fast and cost effective exploration of complex samples of nucleic acids, particularly genomic DNA.

SUMMARY OF THE INVENTION

The present invention provides a flexible and scalable method for analyzing complex samples of nucleic acids, such as genomic DNA. These methods are not limited to any particular type of nucleic acid sample: plant, bacterial, animal (including human) total genome DNA, RNA, cDNA and the like may be analyzed using some or all of the methods disclosed in this invention. The word "DNA" may be used below as an example of a nucleic acid. It is understood that this term includes all nucleic acids, such as DNA and RNA, unless a use below requires a specific type of nucleic acid. This invention provides a powerful tool for analysis of complex nucleic acid samples. From experimental design to isolation of desired fragments and hybridization to an appropriate array, the invention provides for faster, more efficient and less expensive methods of complex nucleic acid analysis.

The present invention provides for novel methods of sample preparation and analysis comprising managing or reducing, in a reproducible manner, the complexity of a nucleic acid sample. The present invention eliminates the need for multiplex PCR, a time intensive and expensive step in most large scale analysis protocols, and for many of the embodiments the step of complexity reduction may be performed entirely in a single tube. The invention further provides for analysis of the sample by hybridization to an array which may be specifically designed to interrogate fragments for particular characteristics, such as, for example, the presence or absence of a polymorphism. The invention further provides for novel methods of using a computer system to model enzymatic reactions in order to determine experimental conditions and/or to design arrays. In a preferred embodiment the invention discloses novel methods of genome-wide polymorphism discovery and genotyping.

In one embodiment of the invention, the step of complexity management of the nucleic acid sample comprises enzymatically cutting the nucleic sample into fragments, separating the fragments and selecting a particular fragment pool. Optionally, the selected fragments are then ligated to adaptor sequences containing PCR primer templates.

In a preferred embodiment, the step of complexity management is performed entirely in a single tube.

In one embodiment of complexity management, a type IIs endonuclease is used to digest the nucleic acid sample and the fragments are selectively ligated to adaptor sequences and then amplified.

In another embodiment, the method of complexity management utilizes two restriction enzymes with different cutting sites and frequencies and two different adaptor sequences.

In another embodiment of the invention, the step of complexity management comprises performing the Arbitrarily Primed Polymerase Chain Reaction (AP PCR) upon the sample.

In another embodiment of the invention, the step of complexity management comprises removing repeated sequences by denaturing and reannealing the DNA and then removing double stranded duplexes.

In another embodiment of the invention, the step of complexity management comprises hybridizing the DNA sample to a magnetic bead which is bound to an oligonucleotide probe containing a desired sequence. This embodiment may further comprise exposing the hybridized sample to a single strand DNA nuclease to remove the single stranded DNA, ligating an adaptor sequence containing a Class II S restriction enzyme site to the resulting duplexed DNA and digesting the duplex with the appropriate Class II S restriction enzyme to release the magnetic bead. This embodiment may or may not comprise amplification of the isolated DNA sequence. Furthermore, the adaptor sequence may or may not be used as a template for the PCR primer. In this embodiment, the adaptor sequence may or may not contain a SNP identification sequence or tag.

In another embodiment, the method of complexity management comprises exposing the DNA sample to a mismatch binding protein and digesting the sample with a 3' to 5' exonuclease and then a single strand DNA nuclease. This embodiment may or may not include the use of a magnetic bead attached to the mismatch binding protein.

BRIEF DESCRIPTION OF THE FIGURES

FIG. 5 depicts type IIs restriction enzymes and their cleavage sites.

FIG. 8 depicts the results of AP PCR on human genomic DNA.

DETAILED DESCRIPTION OF THE PRESENT INVENTION

Figure 1:
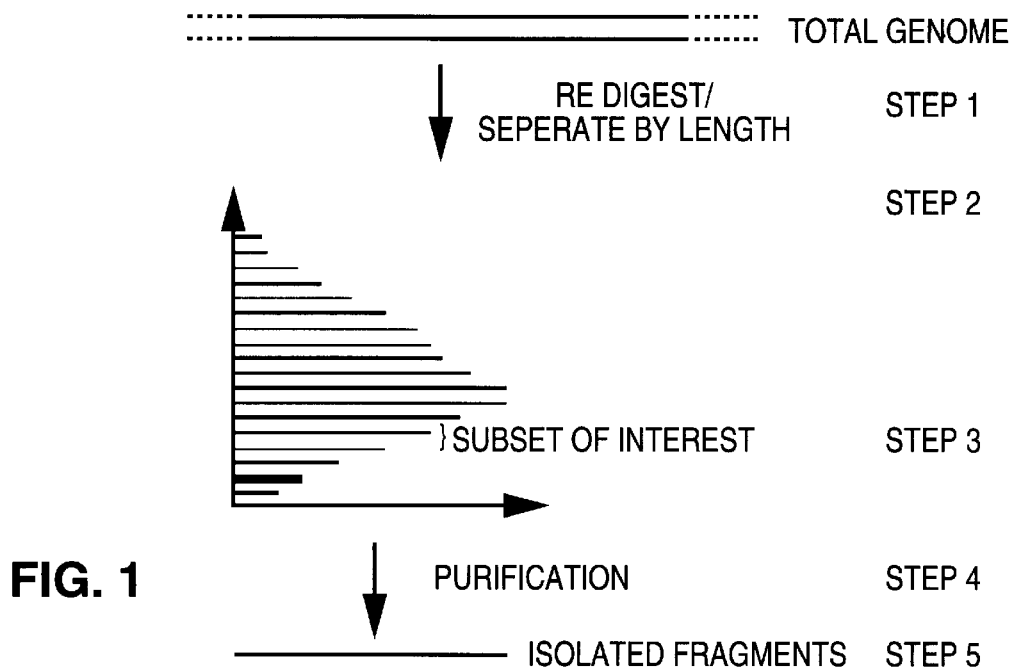
FIG. 1 is a schematic representation of a method of complexity management comprising restriction enzyme digest, fragment separation, and isolation and purification of a fragment size range of interest.

This application relies on the disclosure of other patent applications and literature references. These documents are hereby incorporated by reference in their entireties for all purposes.

Definitions

A "genome" is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

An "oligonucleotide" can be nucleic acid, such as DNA or RNA, and single- or double-stranded. Oligonucleotides can be naturally occurring or synthetic, but are typically prepared by synthetic means. Oligonucleotides can be of any length but are usually at least 5, 10, or 20 bases long and may be up to 20, 50, 100, 1,000, or 5,000 bases long. A polymorphic site can occur within any position of the oligonucleotide. Oligonucleotides can include peptide nucleic acids (PNAS) or analog nucleic acids. See U.S. patent application Ser. No. 08/630,427 filed Apr. 3, 1996.

An array comprises a solid support with nucleic acid probes attached to said support. Arrays typically comprise a plurality of different oligonucleotide probes that are coupled to a surface of a substrate in different known locations. These arrays, also described as "microarrays" or colloquially "chips" have been generally described in the art, for example, U.S. Pat. Nos. 5,143,854, 5445934, 5,744,305, 5,677,195 and PCT Patent Publication Nos. WO 90/15070 and 92/10092, each of which is incorporated by reference in its entirety for all purposes. These arrays may generally be produced using mechanical synthesis methods or light directed synthesis methods which incorporate a combination of photolithographic methods and solid phase synthesis methods. See Fodor et al., Science, 251:767–777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, each of which is hereby incorporated in its entirety by reference for all purposes. Techniques for the synthesis of these arrays using mechanical synthesis methods are described in, e.g., U.S. Pat. No. 5,384,261, incorporated herein by reference in its entirety for all purposes. Although a planar array surface is preferred, the array may be fabricated on a surface of virtually any shape or even a multiplicity of surfaces. Arrays may be nucleic acids on beads, fibers such as fiber optics, glass or any other appropriate substrate, see U.S. Pat. Nos. 5,770,358, 5,789,162, 5,708, 153 and 5,800,992 which are hereby incorporated in their entirety for all purposes. Arrays may be packaged in such a manner as to allow for diagnostics or other manipulation of in an all inclusive device, see for example, U.S. Pat. Nos. 5,856,174 and 5,922,591 incorporated in their entirety by reference for all purposes.

Hybridization probes are oligonucleotides capable of binding in a base-specific manner to a complementary strand of nucleic acid. Such probes include peptide nucleic acids, as described in Nielsen et al., *Science* 254, 1497–1500 (1991), and other nucleic acid analogs and nucleic acid mimetics. See U.S. patent application Ser. No. 08/630,427 filed Apr. 3, 1996.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

An individual is not limited to a human being, but may also include other organisms including but not limited to mammals, plants, bacteria or cells derived from any of the above.

General

The present invention provides for novel methods of sample preparation and analysis involving managing or reducing the complexity of a nucleic acid sample, such as genomic DNA, in a reproducible manner. The invention further provides for analysis of the above sample by hybridization to an array which may be specifically designed to interrogate the desired fragments for particular characteristics, such as, for example, the presence or absence of a polymorphism. The invention further provides for novel methods of using a computer system to model enzymatic reactions in order to determine experimental conditions before conducting any actual experiments. As an example, the present techniques are useful to identify new polymorphisms and to genotype individuals after polymorphisms have been identified.

Generally, the steps of the present invention involve reducing the complexity of a nucleic acid sample using the disclosed techniques alone or in combination. None of these techniques require multiplex PCR and most of them can be performed in a single tube. With one exception (AP PCR), the methods for complexity reduction involve fragmenting the nucleic acid sample, often, but not always by restriction enzyme digest. The resulting fragments, or in the case of AP PCR, PCR products, of interest are then isolated. The isolation steps of the present invention vary but may involve size selection or direct amplification, often adaptor sequences are employed to facilitate isolation. In a preferred embodiment the isolated sequences are then exposed to an array which may or may not have been specifically designed and manufactured to interrogate the isolated sequences. Design of both the complexity management steps and the arrays may be aided by the computer modeling techniques which are also described in the present invention.

Complexity Management

The present invention provides for a number of novel methods of complexity management of nucleic acid samples such as genomic DNA. These methods are disclosed below.

A number of methods disclosed herein require the use of restriction enzymes to fragment the nucleic acid sample. Methods of using a restriction enzyme or enzymes to cut nucleic acids at a large number of sites and selecting a size range of restriction fragments for assay have been shown. This scheme is illustrated in FIG. 1.

Figure 2:
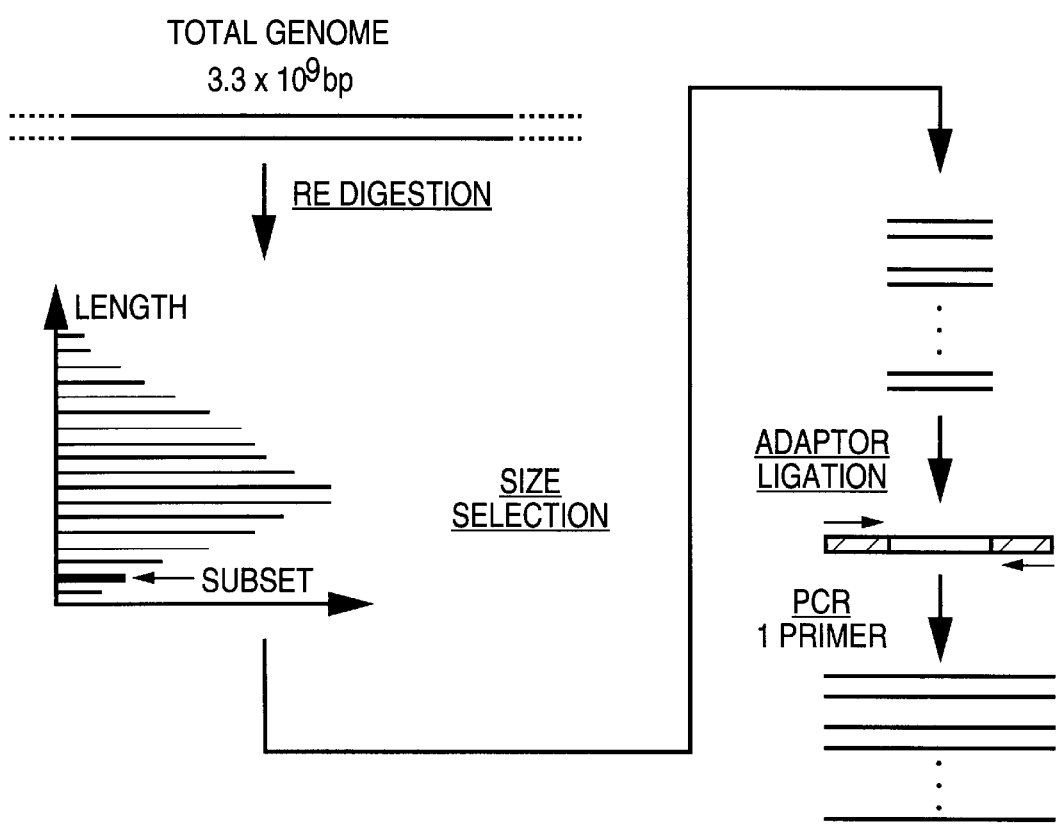
FIG. 2 is a schematic representation of a method of complexity management comprising restriction enzyme digest, fragment separation, isolation and purification of a fragment size range of interest, ligation of an adaptor sequence to the desired fragments and amplification of those fragments.
Figure 3A:
FIG. 3 depicts the effect on complexity of PCR amplification using primers with and without specific nucleotides.
Figure 3A:
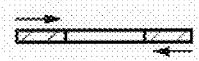
Figure 3B:
Figure 3B:
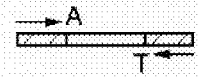
Figure 3C:
Figure 3C:
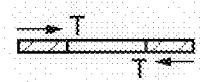

In one embodiment of the invention, schematically illustrated in FIG. 2, restriction enzymes are used to cut the nucleic acids in the sample (FIG. 2, Step 1). In general, a restriction enzyme recognizes a specific nucleotide sequence of four to eight nucleotides (though this number can vary) and cuts a DNA molecule at a specific site. For example, the restriction enzyme Eco RI recognizes the sequence GAATTC and will cut a DNA molecule between the G and the first A. Many different restriction enzymes are known and appropriate restriction enzymes can be chosen for a desired result. For example, restriction enzymes can be purchased from suppliers such as New England Biolabs. Methods for conducting restriction digests will be known to those of skill in the art, but directions for each restriction enzyme are generally supplied with the restriction enzymes themselves. For a thorough explanation of the use of restriction enzymes, see for example, section 5, specifically pages 5.2–5.32 of Sambrook, et al., incorporated by reference above.

After restriction enzyme digestion, the method further requires that the pool of digested DNA fragments be separated by size and that DNA fragments of the desired size be selected (FIG. 2, step 2) and isolated (FIG. 2, Step 3). Methods for separating DNA fragments after a restriction digest will be well known to those of skill in the art. As a non-limiting example, DNA fragments which have been digested with a restriction enzyme may be separated using gel electrophoresis, see for example, Maniatis, section 6. In this technique, DNA fragments are placed in a gel matrix. An electric field is applied across the gel and the DNA fragments migrate towards the positive end. The larger the DNA fragment, the more the fargment's migration is inhibited by the gel matrix. This allows for the separation of the DNA fragments by size. A size marker is run on the gel simultaneously with the DNA fragments so that the fragments of the desired size may be identified and isolated from the gel. Methods for purification of the DNA fragments from the gel matrix are also described in Sambrook et al.

Any other non-destructive method of isolating DNA fragments of the desired size may be employed. For example, size-based chromatography, HPLC, dHPLC or a sucrose density gradient could be used to reduce the DNA pool to those fragments within a particular size range and then this smaller pool could be run on an electrophoresis gel.

After isolation, adaptor sequences are ligated to the fragments. (FIG. 2, Step 4) Adaptor sequences are generally oligonucleotides of at least 5 or 10 bases and preferably no more than 50 or 60 bases in length, however, adaptor sequences may be even longer, up to 100 or 200 bases depending upon the desired result. For example, if the desired outcome is to prevent amplification of a particular fragment, longer adaptor sequences designed to form stem loops or other tertiary structures may be ligated to the fragment. Adaptor sequences may be synthesized using any methods known to those of skill in the art. For the purposes of this invention they may, as options, comprise templates for PCR primers and/or tag or recognition sequences. The design and use of tag sequences is described in U.S. Pat. No. 5,800,992 and U.S. Provisional Patent Application No. 60/140,359, filed Jun. 23, 1999, both of which are incorporated by reference for all purposes. Adaptor sequences may be ligated to either blunt end or sticky end DNA. Methods of ligation will be known to those of skill in the art and are described, for example, in Sambrook et al. Methods include DNase digestion to "nick" the DNA, ligation with ddNTP and the use of polymerase I to fill in gaps or any other methods described in the art.

Further complexity reduction is achieved by adding a specific nucleotide on the 3' end of the PCR primer as illustrated in FIG. 3. The specific nucleotide further reduces the complexity of the resulting DNA pool because only those fragments which have been isolated after restriction enzyme digestion and contain the complement of the specific nucleotide(s) incorporated in the PCR primer will be amplified. FIG. 3A depicts the results of hybridization to an array after enzyme digestion, ligation to an adaptor and PCR amplification. FIGS. 3B and 3C depict the results of hybridization to an array after enzyme digestion, ligation to an adaptor and PCR amplification where the PCR primers incorporated specific nucleotides in the 3' end of the primer. In FIG. 3B the 5' and 3' primers have different specific nucleotides incorporated. In FIG. 3A the 5' and 3' primers have the same nucleotides incorporated. The level of complexity in the isolated pool can be varied depending upon the identity and number of nucleotides incorporated into the PCR primers. A number of embodiments of the present invention involve amplification by PCR. Any of these embodiments may be further modified to reduce complexity using the above disclosed technique.

Various methods of conducting PCR amplification and primer design and construction for PCR amplification will be known to those of skill in the art. PCR is a method by which a specific polynucleotide sequence can be amplified in vitro. PCR is an extremely powerful technique for amplifing specific polynucleotide sequences, including genomic DNA, single-stranded cDNA, and mRNA among others. As described in U.S. Pat. Nos. 4,683,202, 4,683,195, and 4,800, 159 (which are incorporated herein by reference), PCR typically comprises treating separate complementary strands of a target nucleic acid with two oligonucleotide primers to form complementary primer extension products on both strands that act as templates for synthesizing copies of the desired nucleic acid sequences. By repeating the separation and synthesis steps in an automated system, essentially exponential duplication of the target sequences can be achieved. Standard protocols may be found in, for example Sambrook et al. which is hereby incorporated by reference for all purposes.

Figure 4:
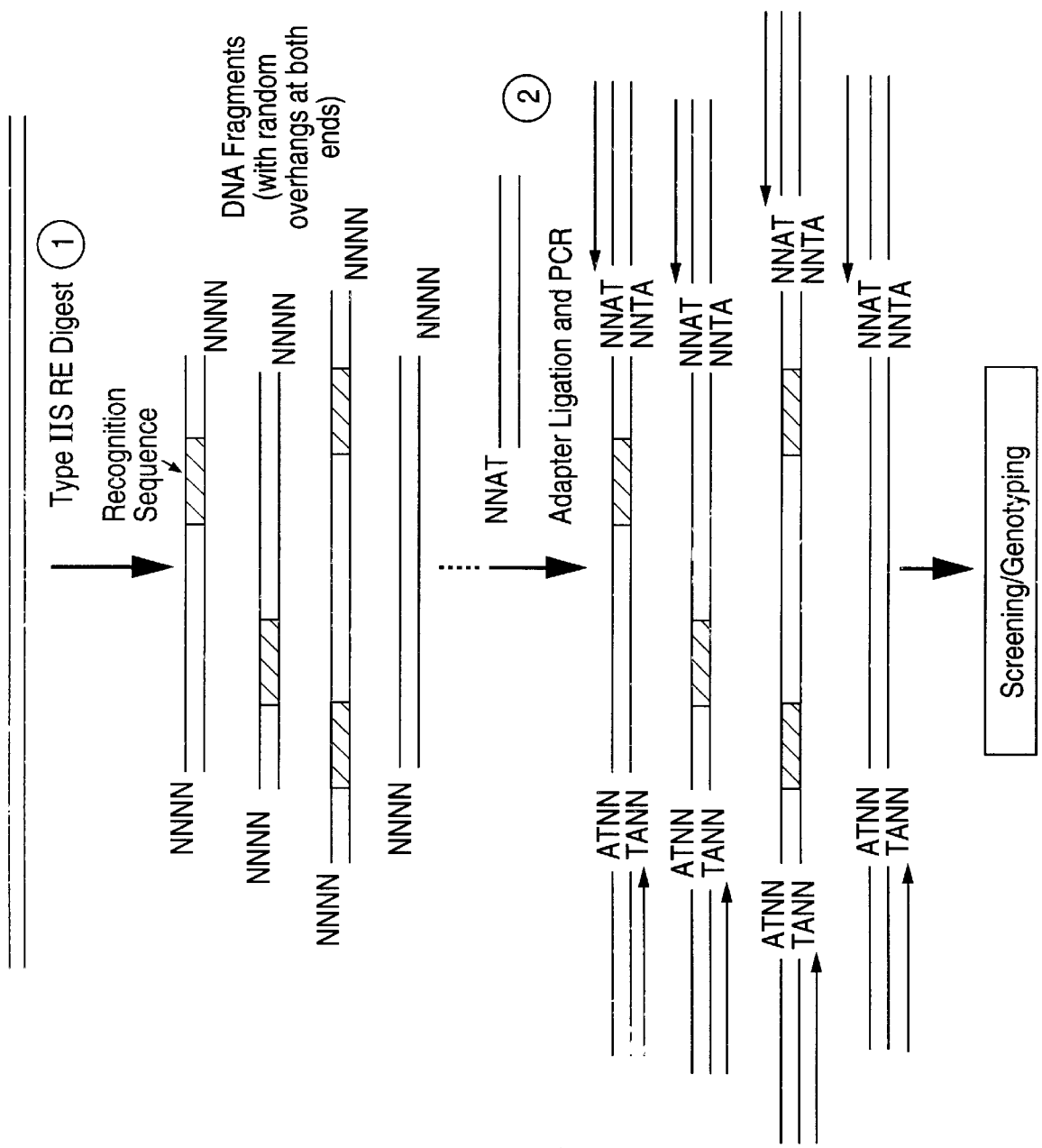
FIG. 4 is a schematic representation of a method of complexity management comprising a type IIs restriction enzyme digest, adaptor sequence ligation and amplification of desired fragments.

In another embodiment, schematically illustrated in FIG. 4, the step of complexity management of the DNA samples comprises digestion with a Type IIs endonuclease thereby creating sticky ends comprised of random nucleic acid sequences. (FIG. 4, Step 1) Type-IIs endonucleases are generally commercially available and are well known in the art. A description of Type IIs endonucleases can be found in U.S. Pat. No. 5,710,000 which is hereby incorporated by reference for all purposes. Like their Type-II counterparts, Type-IIs endonucleases recognize specific sequences of nucleotide base pairs within a double stranded polynucleotide sequence. Upon recognizing that sequence, the endonuclease will cleave the polynucleotide sequence, generally leaving an overhang of one strand of the sequence, or "sticky end."

Type-II endonucleases, however, generally require that the specific recognition site be palindromic. That is, reading in the 5' to 3' direction, the base pair sequence is the same for both strands of the recognition site. For example, the sequence

G-‡-A-A-T-T-C
C-T-T-A-A-‡-G is the recognition site for the Type-II endonuclease EcoRI, where the arrows indicate the cleavage sites in each strand. This sequence is palindromic in that both strands of the sequence, when read in the 5' to 3' direction are the same.

The Type-IIs endonucleases, on the other hand, generally do not require palindromic recognition sequences. Additionally, these Type-IIs endonucleases also generally cleave outside of their recognition sites. For example, the Type-IIs endonuclease EarI recognizes and cleaves in the following manner:

CTCTTCN‡NNNN (SEQ ID NO: 1)
GAGAAGnnnn‡n (SEQ ID NO: 2)

where the recognition sequence is -C-T-C-T-T-C-, N and n represent complementary, ambiguous base pairs and the arrows indicate the cleavage sites in each strand. As the example illustrates, the recognition sequence is non-palindromic, and the cleavage occurs outside of that recogition site.

Specific Type-IIs endonucleases which are useful in the present invention include, e.g., EarI, MnlI, PleI, AlwI, BbsI, BsaI, BsmAI, BspMI, Esp3I, HgaI, SapI, SfaNI, BbvI, BsmFI, FokI, BseRI, HphI and MboII. The activity of these Type-IIs endonucleases is illustrated in FIG. 5, which shows the cleavage and recognition patterns of the Type-IIs endonucleases.

Figure 6A:
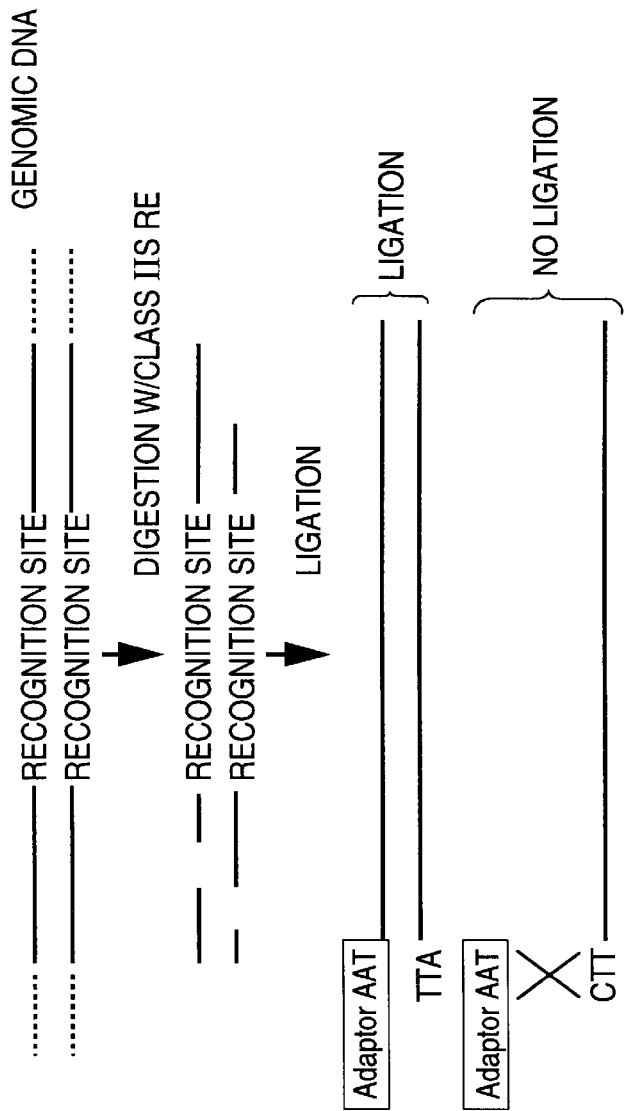
FIG. 6 is a schematic representation of a method of complexity management comprising a type IIs restriction enzyme digest, adaptor sequence ligation and amplification of desired fragments.
Figure 6B:
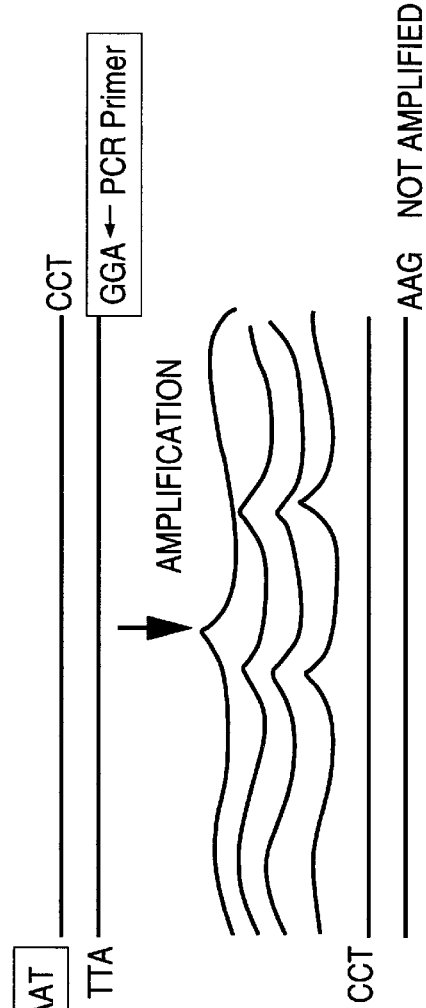

The sticky ends resulting from Type-IIs endonuclease digestion are then ligated to adaptor sequences (FIG. 4, Step 2) Those of skill in the art will be familiar with methods of ligation. Standard protocols can be found in, for example, Sambrook et al., hereby incorporated by reference for all purposes. Only those fragments containing the adaptor sequence are isolated. (FIG. 6).

In addition to those methods of isolation discussed above, methods of isolation which take advantage of unique tag sequences which may be constructed in the adaptor sequences may be employed. These tag sequences may or may not be used as PCR primer templates. Fragments containing these tags can then be segregated from other non-tag bearing sequences using various methods of hybridization or any of the methods described in the above referenced application.

Figure 18:
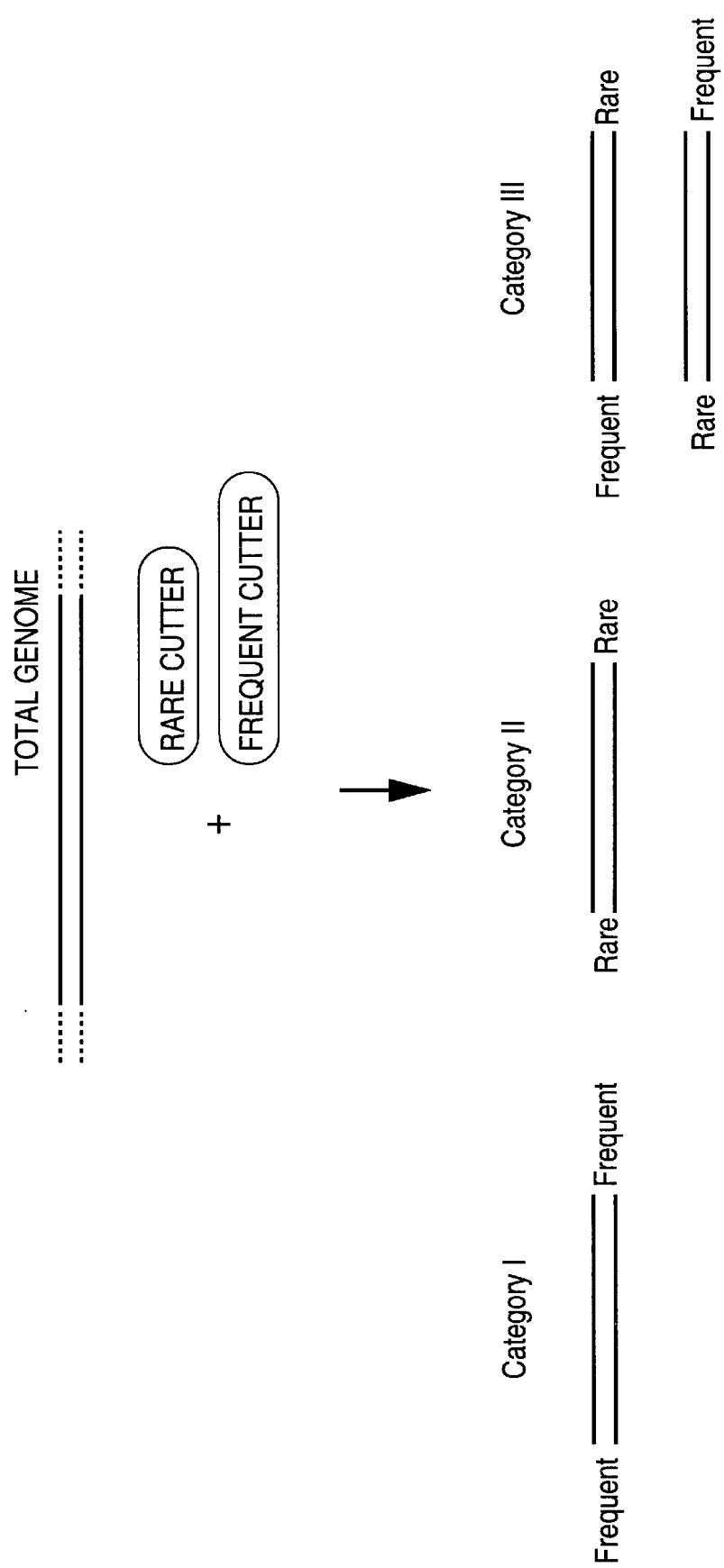
FIG. 18 is a schematic of a method of complexity reduction comprising digesting the DNA sample with one enzyme with a relatively rare restriction site and a second enzyme with a relatively frequent restriction site.

In another embodiment, depicted in FIG. 18, the method of complexity reduction comprises digesting the DNA sample with two different restriction enzymes. The first restriction enzyme is a frequent base cutter, such as MSE I which has a four base recognition site. The second restriction enzyme is a rare base cutter, such as Eco RI, which has a 6 base recognition site. This results in three possible categories of fragments; (most common) those which have been cut on both ends with the frequent base cutter, (least common) those which have been cut on both ends with the rare base cutter, and those which have been cut on one end with the frequent base cutter and on one end with the rare base cutter. Adaptors are ligated to the fragments and PCR primers are designed such that only those fragments which fall into the desired category or categories are amplified. This technique, employed with a six base cutter and a four base cutter can reduce complexity 8-fold when only those fragments from the latter category are amplified. Other combinations of restriction enzymes may be employed to achieve the desired level of complexity.

Figure 10:
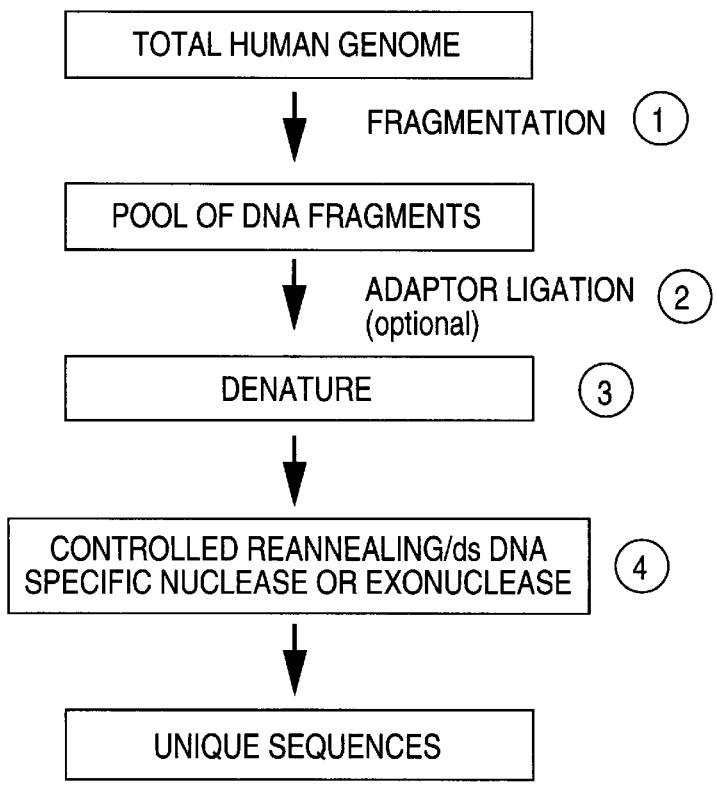
FIG. 10 is a schematic representation of a method of complexity management comprising removing repetitive sequences by denaturing and reannealing genomic DNA.

In another embodiment, the step of complexity management comprises removing repetitive sequences. FIG. 10 depicts a schematic representation of this embodiment. The nucleic acid sample is first fragmented. (FIG. 10, Step 1)

Various methods of fragmenting DNA will be known to those of skill in the art. These methods may be, for example, either chemical or physical in nature. Chemical fragmentation may include partial degradation with a DNAse, partial depurination with acid, the use of restriction enzymes or other enzymes which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale.

In a preferred embodiment adaptor sequences are ligated to the resulting fragments. (FIG. 10, Step 2) The fragments with or without adaptor sequences are then denatured. (FIG. 10, Step 3) Methods of denaturation will be will known to those of skill in the art. After denaturation, the fragments are then allowed to reanneal. (FIG. 10, Step 4) Annealing conditions may be altered as appropriate to obtain the level of repetitive sequence removal desired. Finally, double stranded sequences are removed (FIG. 10, Step 4). Methods of removing double stranded sequences will be known to those of skill in the art and may include without limitation, methods of digesting double stranded DNA such as double strand specific nucleases and exonucleases or methods of physical separation including, without limitation gel based electrophoresis or size chromatography.

Figure 7:
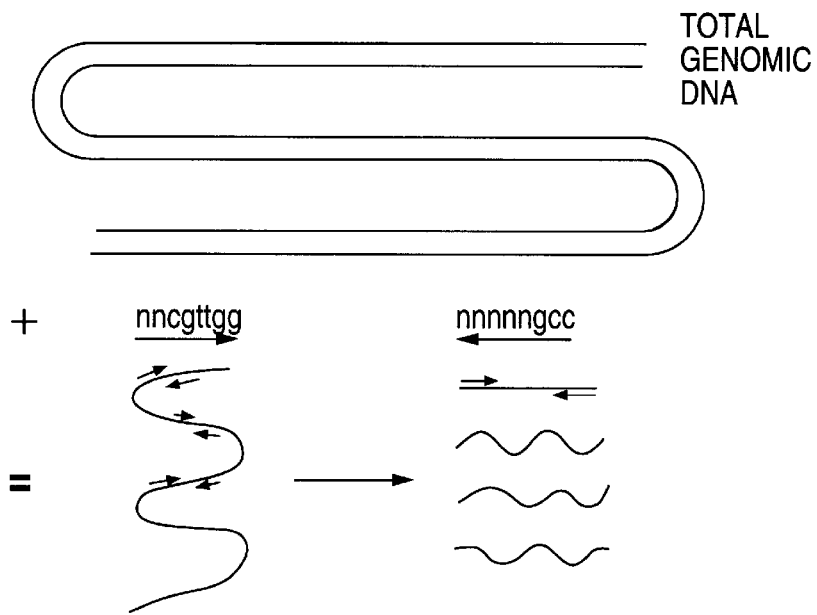
FIG. 7 is a schematic representation of a method of complexity management comprising AP PCR.
Figure 9A:
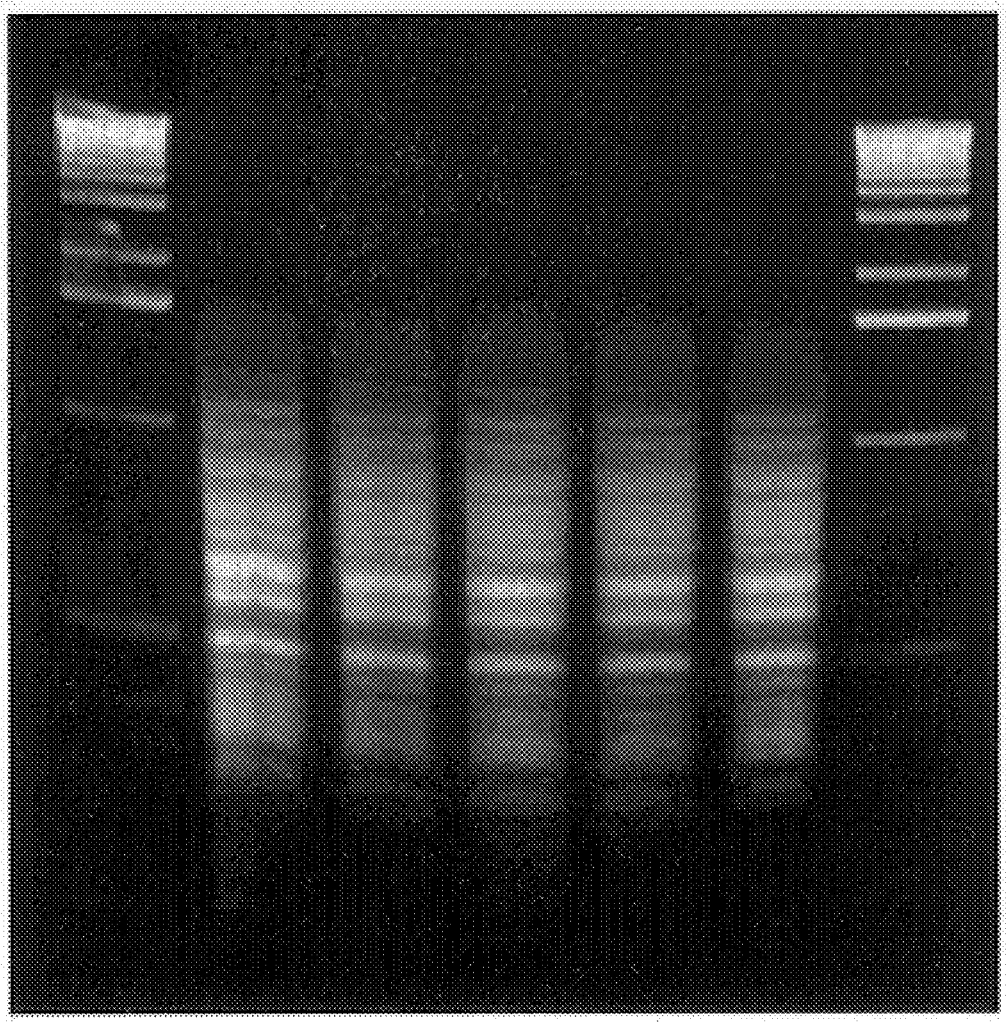
FIG. 9 depicts the reproducibility of AP PCR.
Figure 9B:
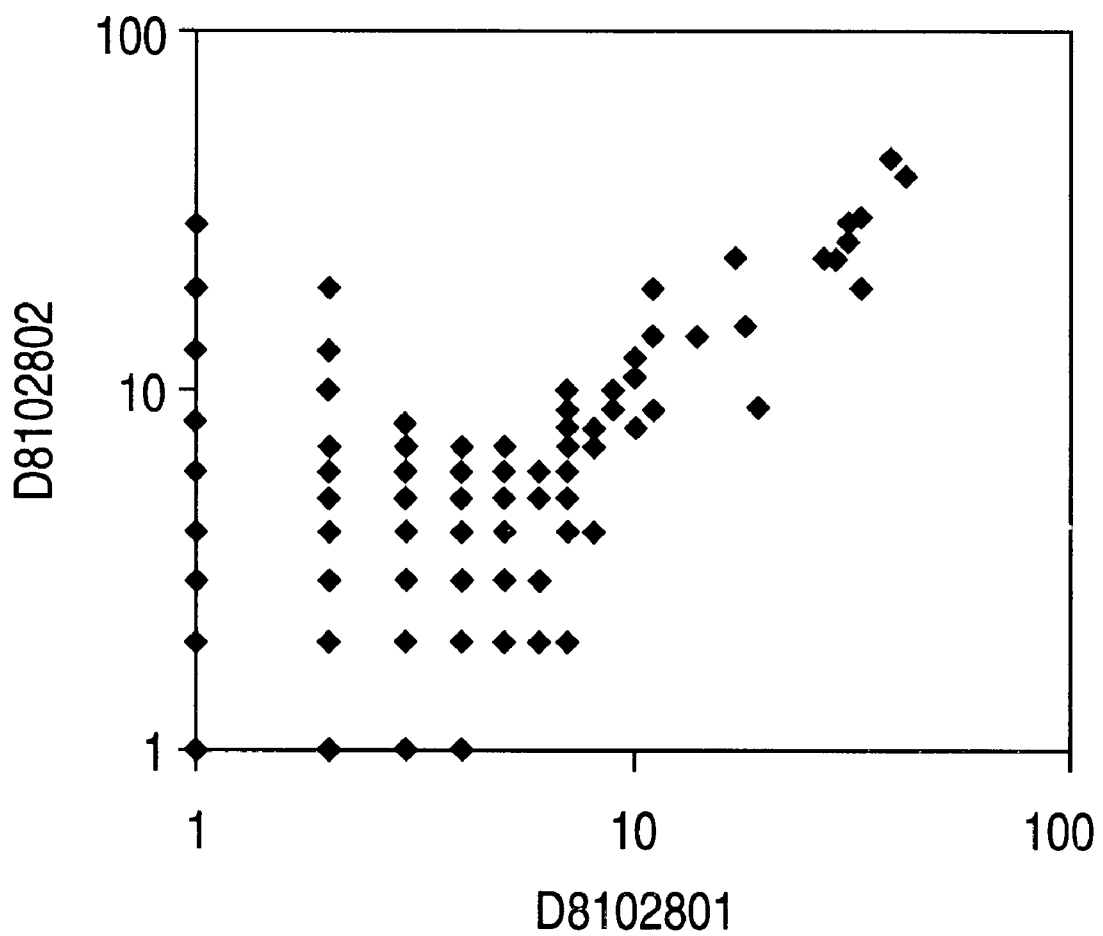

In another embodiment, the step of complexity management comprises performing an arbitrarily primed polymerase chain reaction (AP PCR) upon the sample. AP PCR is described in U.S. Pat. No. 5,487,985 which is hereby incorporated by reference in its entirety for all purposes. FIG. 7 depicts a schematic illustration of this embodiment. Performing AP PCR with random primers which have specific nucleotides incorporated into the primers produces a reduced representation of genomic DNA in a reproducible manner. FIG. 8 shows the level of complexity reduction of human genomic DNA resulting from AP PCR with various primers. Column 1 lists the primer name. Column 2 lists the primer sequence. Column 3 lists the annealing temperature. Column 4 lists the polymerase used. Column 5 lists the number correlated to a specific gene on the Hum6.8K GeneChip(R) probe array (Affymetrix, Inc. Santa Clara, Calif.). Column 6 lists the percentage of the human genes on the Hum6.8K GeneChip(R) probe array found by fragments whose complexity has been reduced by this method. FIG. 9 shows the reproducibility of AP PCR. Independently prepared samples were subjected to AP PCR using the same primers. The gel bands show that the level of reproducibility between the samples is very high.

Primers may be designed using standard techniques. For example, a computer program is available on the internet at the Operon Technologies, Inc. website. The Operon Oligo Toolkit allows a user to input a potential primer sequence into the webform. The site will instantly calculate a variety of attributes for the oligonucleotide including molecular weight, GC content, Tm, and primer-dimer sets. You may also plot the oligonucletoide against a second sequence. PCR amplification techniques are described above in this application and will be well known to those of skill in the art.

In another embodiment of the invention, the method reducing the complexity of a nucleic acid sample comprises hybridizing the sample to a nucleic acid probe containing a desired sequence which is bound to a solid support, such as a magnetic bead. For a description of hybridization of nucleic acids to solid supports, see U.S. Pat No. 5,800,992 incorporated by reference above. This sequence may comprise, for example, a sequence containing a SNP, a cDNA fragment, a chromosome fragment, a subset of genomic DNA or a subset of a library. The sequence may comprise as few as 16 nucleotides and may comprise as many as 2,000, 3,000, 5,000 or more nucleotides in length. Methods of designing and making oligonucleotide probes will be well known to those of skill in the art. In one embodiment, the probe may contain a template sequence for a PCR primer. Solid supports suitable for the attachment of nucleic acid probe sequences will be well known to those of skill in the art but may include, glass beads, magnetic beads, and/or planar surfaces. Magnetic beads are commercially available from, for example, Dynal (Oslo, Norway). The nucleic acid probes may be synthesized directly on the solid support or attached to the support as a full length sequence. Protocols for attaching magnetic beads to probes are included in U.S. Pat. No. 5,512,439 which is hereby incorporated by reference for all purposes. Standard hybridization protocols as discussed above may be employed.

Figure 11:
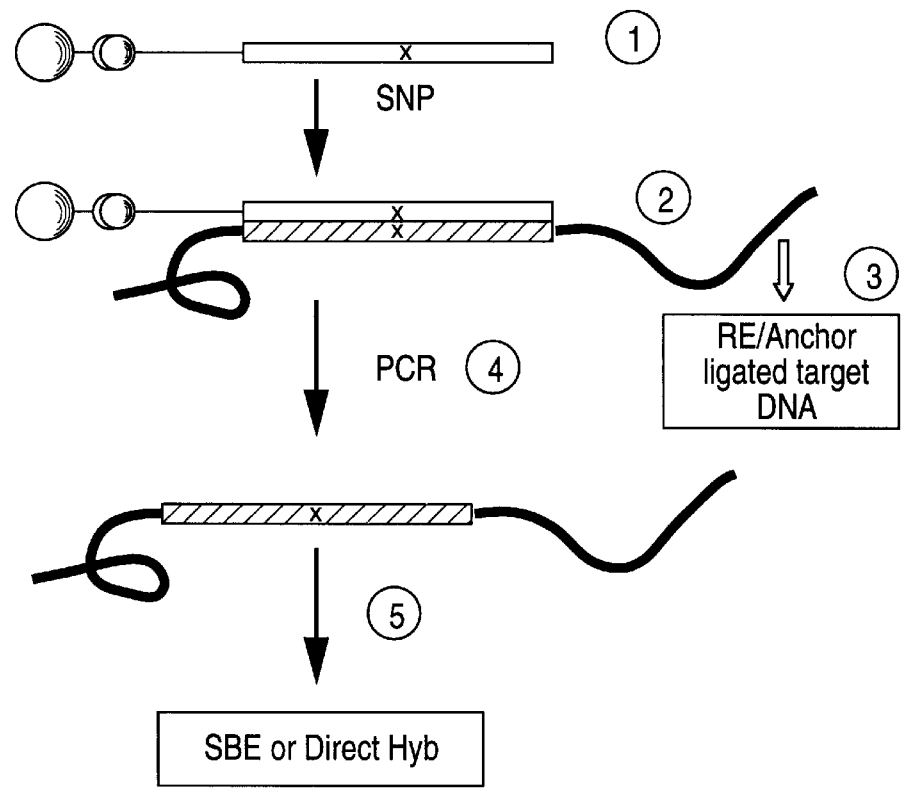
FIG. 11 is a schematic representation of a method of complexity management comprising hybridizing a probe sequence attached to a magnetic bead to a pool of fractionated DNA.

FIG. 11 depicts a schematic representation of one example of the above embodiment, wherein the complexity management step is utilized to facilitate genome wide genotyping. Much of the cost of genotyping comes from multiplex PCR. In this embodiment, the entire sample preparation can be performed in a single tube without the need for multiplex PCR. Because the desired result is to genotype a DNA sample, the desired sequence in FIG. 11 contains a polymorphism. The oligonucleotide comprises 32 bases with the SNP in the center. A magnetic bead is attached to the oligonucleotide probe. (FIG. 11, step 1) The probe is then exposed to, for example, fractionated genomic DNA. (FIG. 11, step 2). Adaptor sequences are ligated to both ends of the fragments. (FIG. 11, step 3). The fragments are then amplified (FIG. 11, step 4) and the PCR product containing the desired polymorphism may then be analyzed by various methods including, for example, hybridization to an array or single base extension (SBE). SBE is described in, for example U.S. Provisional Application 60/140,359 which is hereby incorporated by reference in its entirety for all purposes.

The method may further comprise exposing the hybridized sample to a single strand DNA nuclease to remove the single stranded DNA. This embodiment may further comprise ligating an adaptor sequence containing a Class II S restriction enzyme site to resulting duplexed DNA and digesting the duplex with the appropriate Class II S restriction enzyme to release the attached sequences. The sequences are then isolated and a second adaptor sequence is ligated to the complex and the sequences are amplified.

Figure 12:
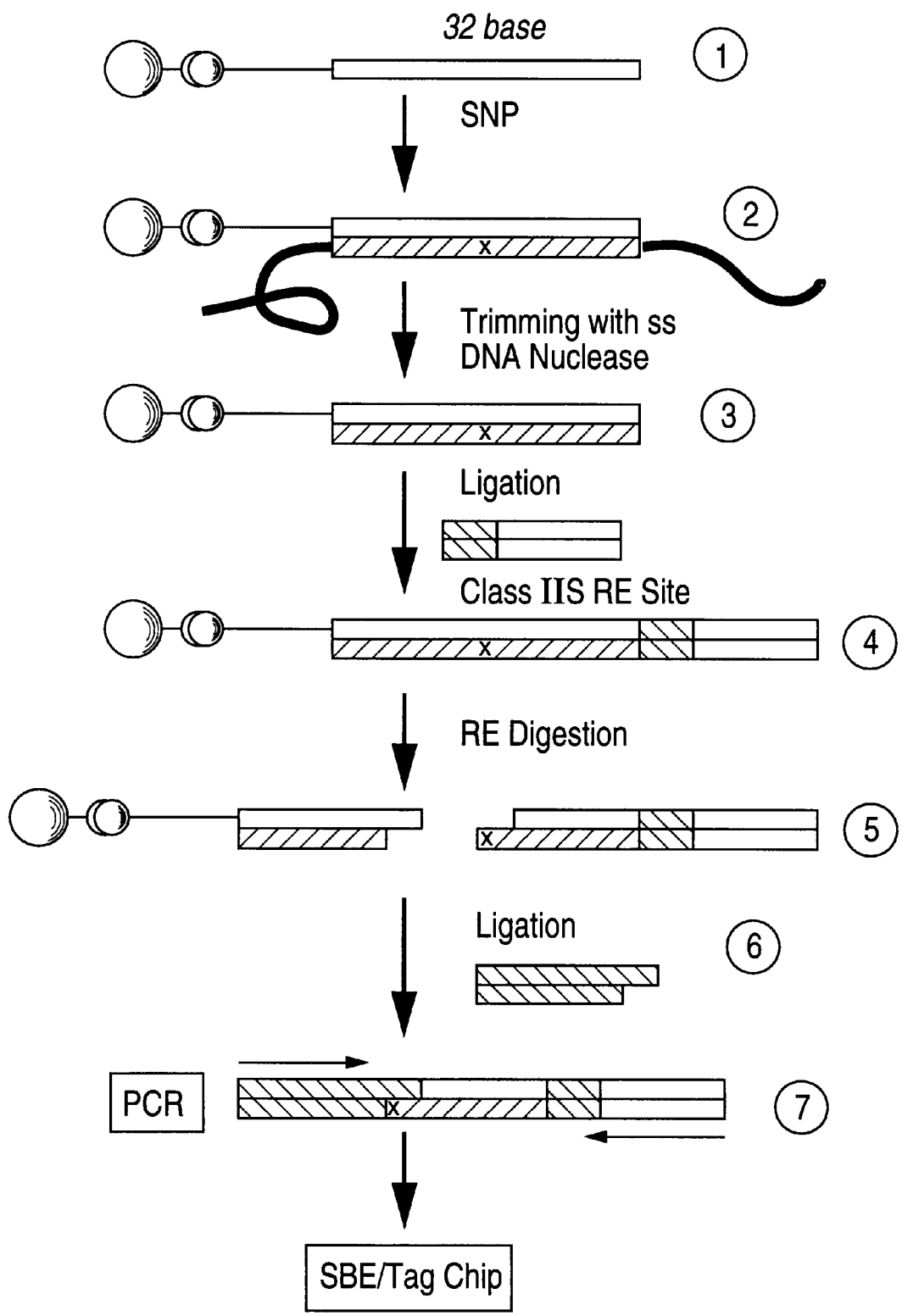
FIG. 12 is a schematic representation of a method of complexity management comprising hybridizing a probe sequence bound to a magnetic bead to a pool of fractionated DNA, ligating an adaptor sequence containing a class IIs restriction enzyme site to the DNA/probe duplex, digesting the duplex, ligating a second adaptor sequence to the duplex and amplifying.
Figure 13:
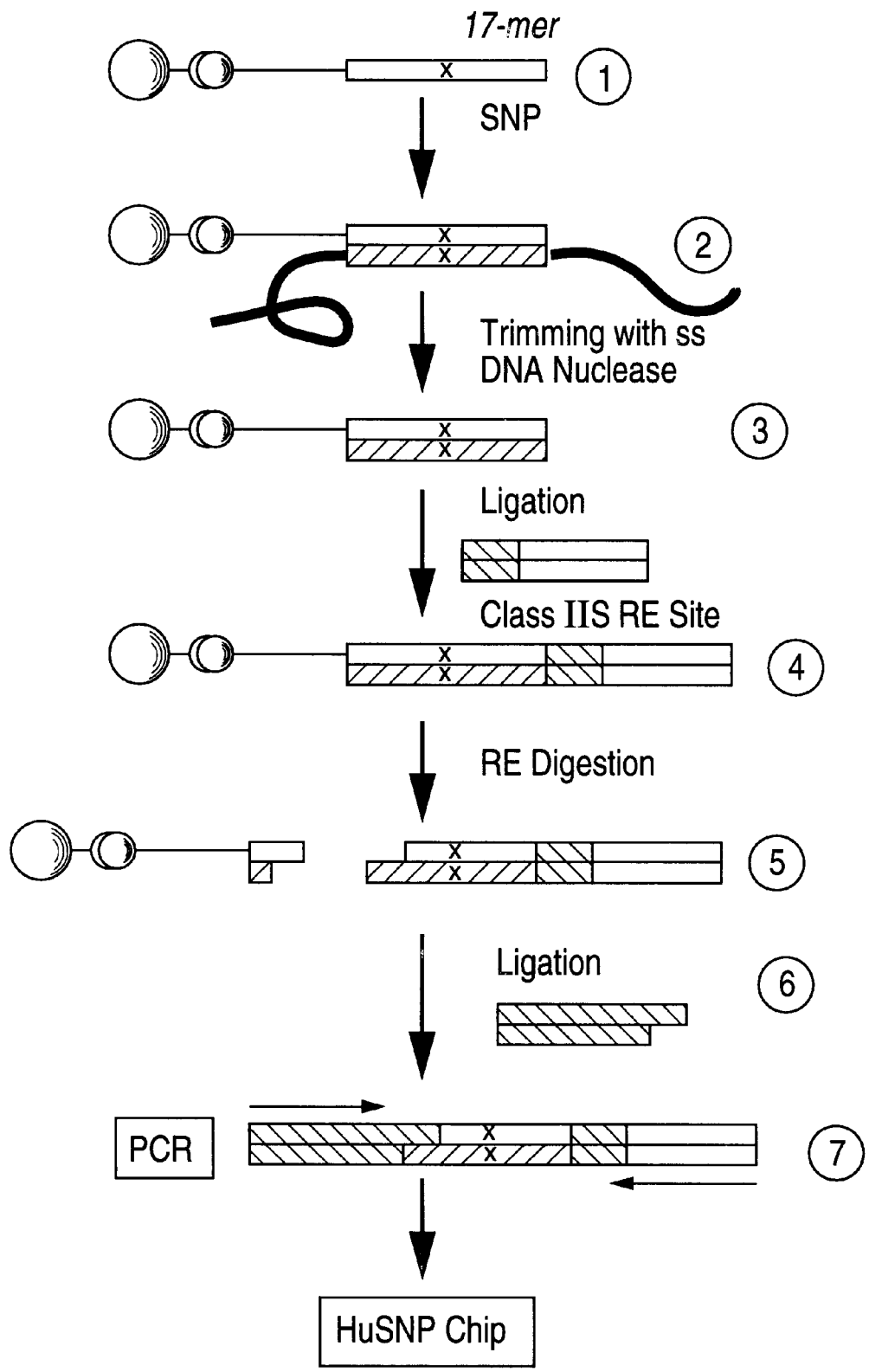
FIG. 13 is a schematic representation of a method of complexity management comprising hybridizing a probe sequence bound to a magnetic bead to a pool of fractionated DNA, ligating an adaptor sequence containing a class IIs restriction enzyme site to the DNA/probe duplex, digesting the duplex, ligating a second adaptor sequence to the duplex and amplifying.

FIGS. 12 and 13 depict schematic representations of an embodiment comprising the use of ClassIIs endonucleases. Both figures depict methods which may be employed for single tube genotyping without the need for multiplex PCR. In FIGS. 12 and 13, the desired sequence is a SNP. The oligonucleotide probe in FIG. 12 is 32 bases long and in FIG. 13 is 17 bases long. In both figures the SNP is in the center of the oligonucleotide. The oligonucleotide probe is bound to a magnetic bead. (FIGS. 12 and 13, step 1). The probe is then hybridized to fragmented genomic DNA (FIGS. 12 and 13, step 2). Single stranded DNA is digested with a single strand DNA nuclease leaving a DNA duplex attached to the magnetic bead. (FIGS. 12 and 13, step 3). An adaptor sequence is then ligated to the duplex. The adaptor sequence contains a Class IIS restriction site. The probe length and Class IIS endonuclease are chosen such that the site where the duplex is cut is between the SNP and the magnetic bead. In FIG. 12 the Class IIS endonuclease cuts directly adjacent to the SNP site, such that the SNP is part of the sticky end left by the endonuclease digestion. (FIG. 12, step 5) In FIG. 13 the endonuclease cuts closer to the magnetic bead, leaving a number of bases between the sticky end and the SNP site. (FIG. 13, step 5) In either case, the magnetic bead is released and the sequences are isolated. Adaptor sequences are then ligated to the sticky ends. (FIGS. 12 and 13, step 6) In both FIGS. 12 and 13 the adaptor sequences contain templates for PCR probes. The fragments containing the SNP are then amplified (FIGS. 12 and 13, step 7) and the PCR products may be analyzed in a number of different methods including hybridization to an array designed to detect SNPs or SBE.

Figure 14:
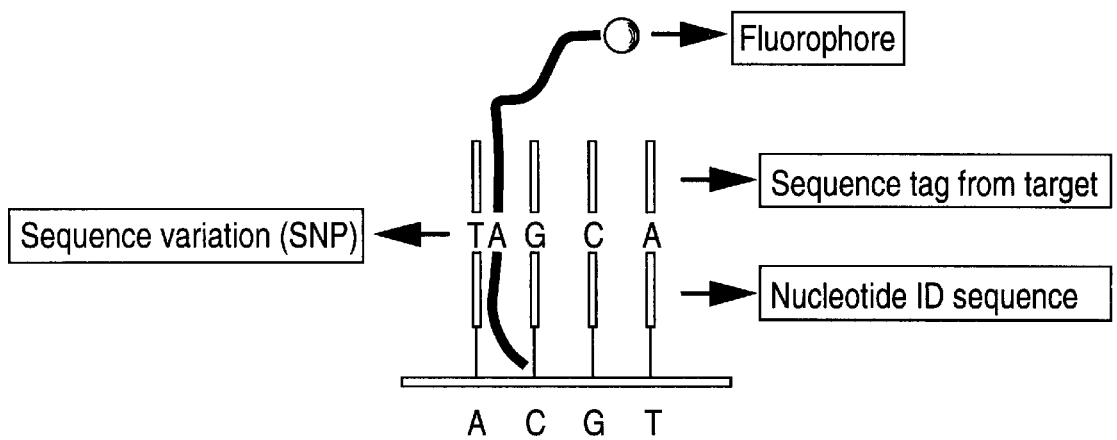
FIG. 14 depicts a chimeric probe array.
Figure 15:
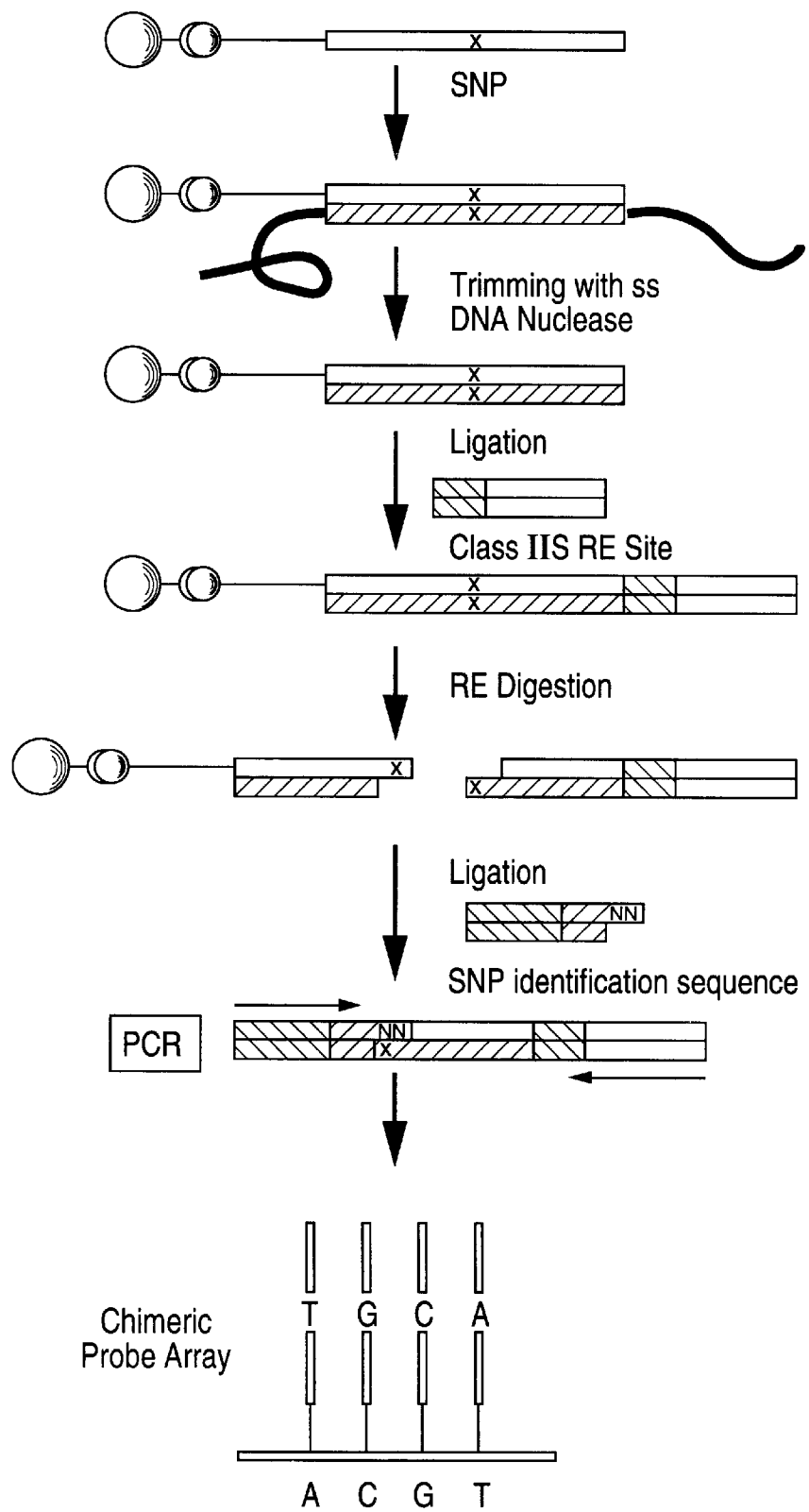
FIG. 15 is a schematic representation of a method of complexity management comprising hybridizing a probe sequence attached to a magnetic bead to a pool of fractionated DNA, ligating an adaptor sequence containing a class IIs restriction enzyme site to the DNA/probe duplex, digesting the duplex, ligating a second adaptor sequence to the duplex, amplifying and hybridizing the amplicons to a chimeric probe array.

In this embodiment, the adaptor sequence may further comprise a SNP identification sequence or tag. In this case, the array to which the PCR products are hybridized may be a generic tag array as described in the above referenced U.S. Pat. No. 5,800,992 and U.S. Provisional Patent Application 60/140,359 or a chimeric probe array (FIG. 14). A chimeric probe array contains probes which interrogate both for particular sequences characteristic of a genotype as well as for artificial sequences which have been ligated to specific fragments in the sample pool. This allows for higher specificity of hybridization and better differentiation between probes. This embodiment is depicted in FIG. 15.

Figure 16:
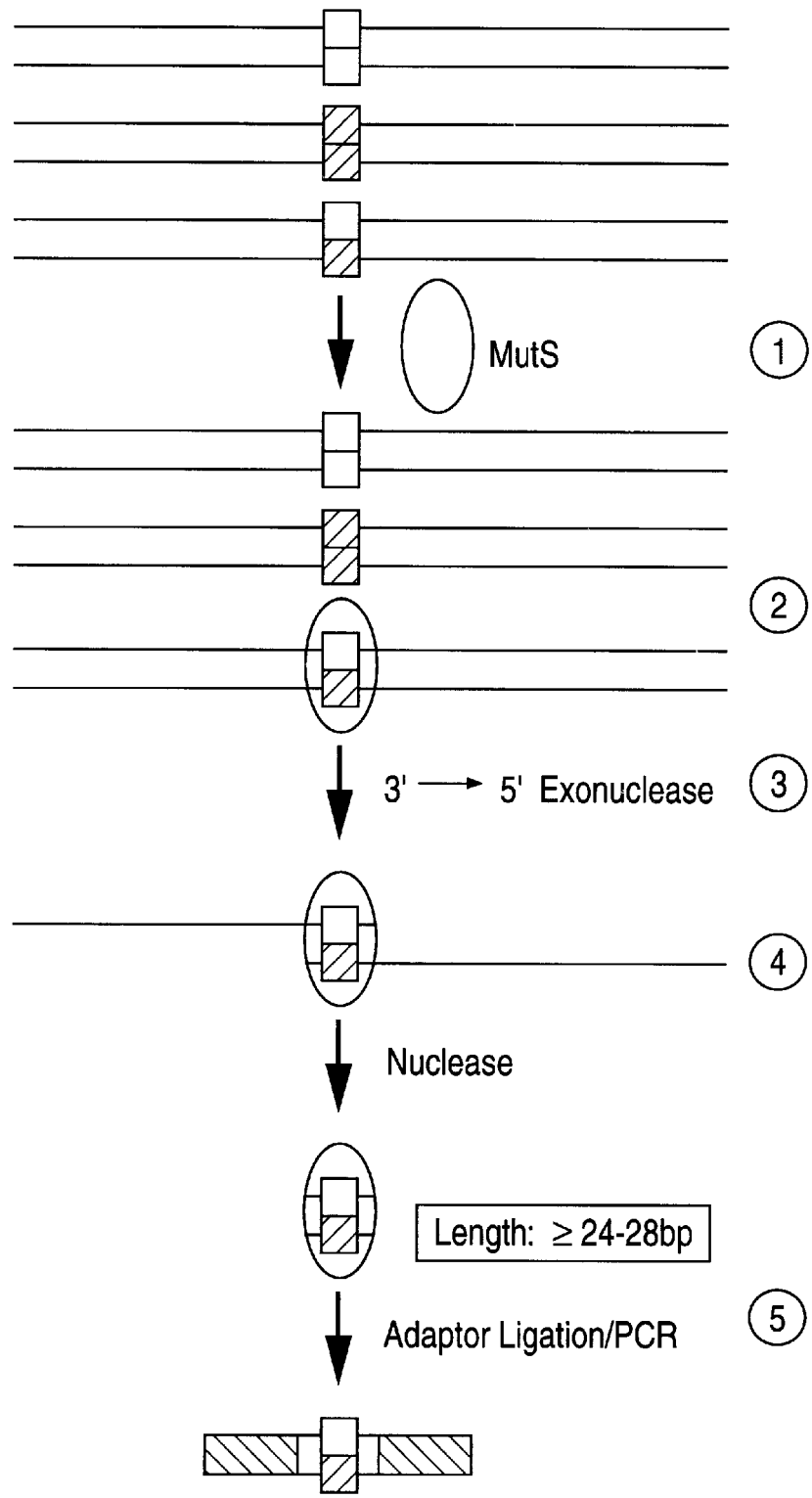
FIG. 16 is a schematic representation of a method of complexity management comprising hybridizing a mismatch binding protein to DNA containing a polymorphism and isolating the region containing the polymorphism.
Figure 17:
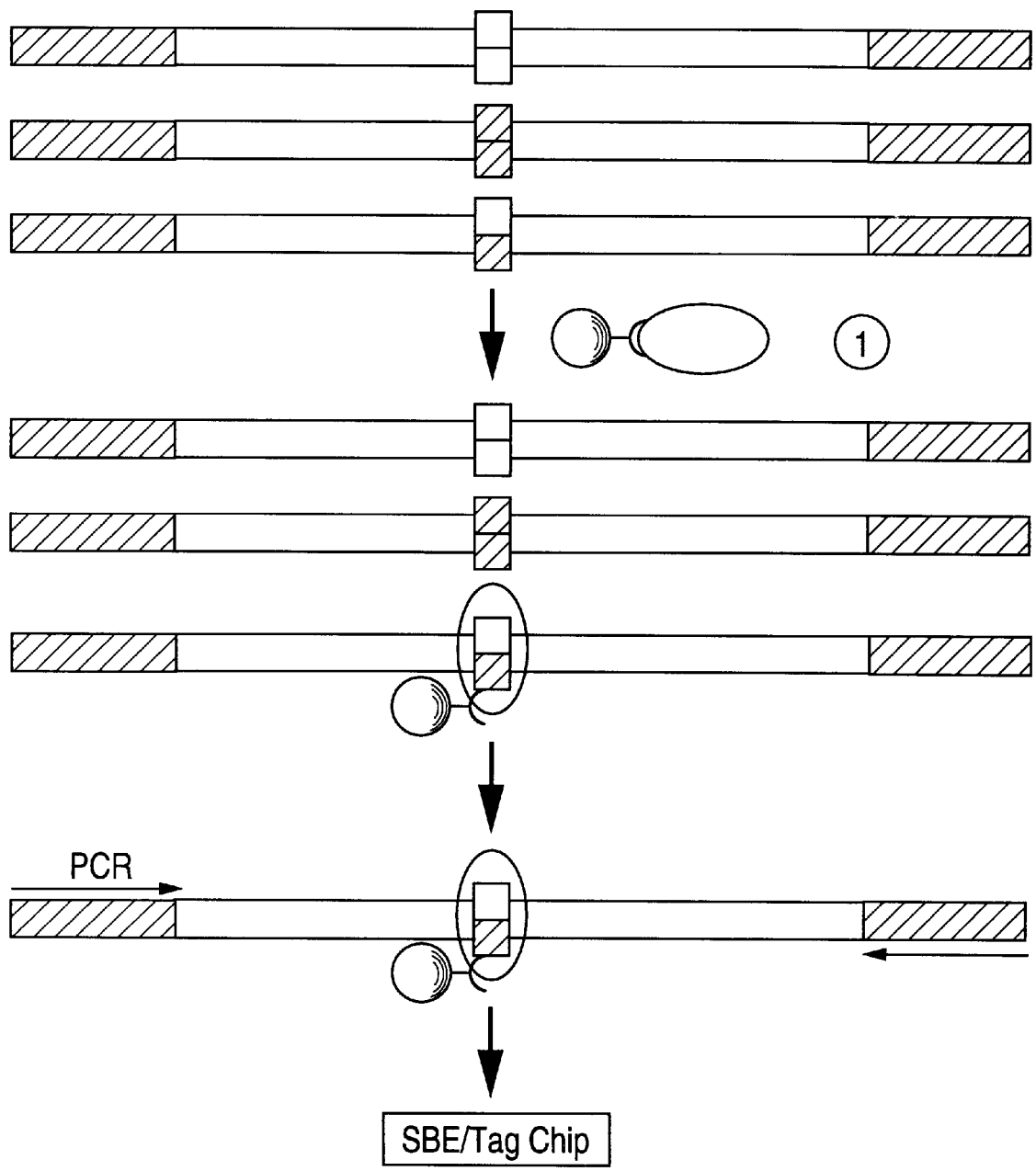
FIG. 17 is a schematic representation of a method of complexity management comprising attaching a magnetic bead to the mismatch binding protein of FIG. 16.

In another embodiment, depicted in FIG. 16 the method of complexity reduction comprises hybridizing the DNA sample to a mismatch binding protein. FIG. 16, step 2. Mismatch binding proteins are described in Wagner R. and Radman, M. (1995) "Methods: A Companion to Methods in Enzymology" 7, 199–203 which is hereby incorporated by reference in its entirety for all purposes. Mismatch binding proteins preferentially bind to DNA duplexes which contain sequence mismatches. This allows for a relatively simple and rapid method to locate and identify SNPs. In this embodiment no prior knowledge of the SNP is required. Mismatch binding proteins are commercially available through GeneCheck (Ft. Collins, Colo.). In a further embodiment, depicted in FIG. 17, magnetic beads are attached to the mismatch binding proteins. Mismatch binding proteins attached to magnetic beads are commercially available through GeneCheck (Ft. Collins, Colo.). After hybridization the sample is digested with a 3' to 5' exonuclease (FIG. 16, step 3). Remaining single stranded DNA is then removed with a nuclease (FIG. 16, step 4).

If it is desired to cut the duplex at the mismatch, then the enzyme resolvase may be used. See U.S. Pat. Nos. 5,958, 692, 5,871,911 and 5,876,941 (each of which is incorporated by reference in their entireties for all purposes) for a description of various methods of cleaving nucleic acids. The resolvases (e.g. X-solvases of yeast and bacteriophage T4, Jensch et al. EMBO J. 8, 4325 (1989)) are nucleolytic enzymes capable of catalyzing the resolution of branched DNA intermediates (e.g., DNA cruciforms) which can involve hundreds of nucleotides. In general, these enzymes are active close to the site of DNA distortion (Bhattacharyya et al., J. Mol. Biol., 221, 1191, (1991)). T4 Endonuclease VII, the product of gene 49 of bacteriophage T4 (Kleff et al., The EMBO J. 7, 1527, (1988)) is a resolvase (West, Annu. Rev. Biochem. 61, 603, (1992)) which was first shown to resolve Holliday-structures (Mizuuchi et al., Cell 29, 357, (1982)). T4 Endonuclease VII has been shown to recognize DNA cruciforms (Bhattacharyya et al., supra; Mizuuchi et al., supra) and DNA loops (Kleff et al., supra), and it may be involved in patch repair. Bacteriophage T7 Endonuclease I has also been shown to recognize and cleave DNA cruciforms (West, Ann. Rev. Biochem. 61, 603, (1992)). Eukaryotic resolvases, particularly from the yeast Saccharomyces cerevisiae, have been shown to recognize and cleave cruciform DNA (West, supra; Jensch, et al., EMBO J. 8, 4325 (1989)). Other nucleases are known which recognize and cleave DNA mismatches. For example, S1 nuclease is capable of recognizing and cleaving DNA mismatches formed when a test DNA and a control DNA are annealed to form a heteroduplex (Shenk et al., Proc. Natl. Acad. Sci. 72, 989, (1975)). The Nut Y repair protein of *E. coli* is also capable of detecting and cleaving DNA mismatches.

Computer Implemented Analysis

In another embodiment a computer system is used to model the reactions discussed above to aid the user in selecting the correct experimental conditions. In this embodiment, the sequence of the DNA sample must be known. A computer program queries an electronic database containing the sequence of the DNA sample looking for sites which will be recognized by the enzyme being used. The method of modeling experiments can be employed for a wide variety of experiments.

In one embodiment, the user can run multiple experiments altering various conditions. For example, if a user desires to isolate a particular sequence of interest in a fragment which has been digested with a restriction enzyme, the user can have the computer model the possible outcomes using a wide variety of restriction enzymes. The particular sequence which is selected may be chosen by specific criteria, i.e. because the region is believed to be associated with specific genes, polymorphisms, or phenotypes for example, or may be chosen at random. The user can then select the restriction enzyme which, for example, isolates the desired sequence in a fragment of unique size. Additionally or alternatively, if the user desires to reduce complexity using the type IIS nuclease/ligation technique described above, the user can experiment with the length and sequence of the adaptors to determine the optimal sequence for the adaptors' "sticky" ends. This enables the user to be confident that they will obtain a fragment containing a particular sequence of interest or to fine tune the level of complexity in the DNA pool. In another embodiment, a user could model the kinetics of the denaturing, reannealing technique for removal of repeated sequences discussed above to determine the conditions which allow for the desired result. For example, a user may desire the removal of only a certain percentage of repeated sequences.

For example, virtual restriction digests may be performed by querying an electronic database which contains the sequence of DNA of interest. Because the database contains the nucleic acid sequence and restriction enzymes cut at known locations based on the DNA sequence, one can easily predict the sequence and size of fragments which will result from a restriction digest of the DNA. Ideally, restriction enzymes which produce no two fragments of the same or very similar size are desired. Combinations of restriction enzymes may be employed. Those of skill in the art will be familiar with electronic databases of DNA sequences. GenBank, for example, contains approximately 2,570,000,000 nucleic acid bases in 3,525,000 sequence records as of April 1999. A computer program searches the electronic database for a sequence which suits the requirements of the particular restriction enzyme. For example, the restriction enzyme Eco RI recognizes the sequence GAATTC and will cut a DNA molecule between the G and the first A. The computer program will query the chosen sequence for any occurences of the sequence GAATTC and mark the site where the restriction enzyme will cut. The program will then provide the user with a display of the resulting fragments.

Exhibit 1 is an example of a program to conduct this type of virtual enzyme digestion. Exhibit 2 is an example of a program to virtually model the ligation of two sequences to each other.

In another embodiment, the method of modeling experiments in a computer system can be used to design probe arrays. A database may be interrogated for any desired sequence, for example, a polymorphism. Computer modeled reactions are then performed to help determine the method for isolating a fragment of DNA containing the sequence of interest. These methods may comprise any of the methods described above, alone or in combination. Arrays are then constructed which are designed to interrogate the resulting fragments. It is important to note that for the purpose of designing arrays, the virtual reactions need not be performed flawlessly, since the arrays may contain hundreds of thousands of sequences.

One embodiment of the invention relies on the use of virtual reactions to predetermine the sequence of chosen DNA fragments which have subjected to various procedures. The sequence information for the chosen fragments is then used to design the probes which are to be attached to DNA arrays. Arrays may be designed and manufactured in any number of ways. For example, DNA arrays may be synthesized directly onto a solid support using methods described in, for example U.S. Pat. Nos. 5,837,832, 5,744,305 and 5,800,992 and WO95/11995 herein incorporated by reference for all purposes. See also, Fodor et al., Science, 251:767–777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, each of which is hereby incorporated in its entirety by reference for all purposes. Techniques for the synthesis of these arrays using mechanical synthesis methods are described in, e.g., U.S. Pat. No. 5,384,261, incorporated herein by reference in its entirety for all purposes Briefly, U.S. Pat. No. 5,837,832 describes a tiling method for array fabrication whereby probes are synthesized on a solid support. These arrays comprise a set of oligonucleotide probes such that, for each base in a specific reference sequence, the set includes a probe (called the "wild-type" or "WT" probe) that is exactly complementary to a section of the sequence of the chosen fragment including the base of interest and four additional probes (called "substitution probes"), which are identical to the WT probe except that the base of interest has been replaced by one of a predetermined set (typically 4) of nucleotides. Probes may be synthesized to query each base in the sequence of the chosen fragment. Target nucleic acid sequences which hybridize to a probe on the array which contain a substitution probe indicate the presence of a single nucleotide polymorphism. Other applications describing methods of designing tiling arrays include: U.S. Pat. Nos. 5,858,659, and 5,861,242 each of which is incorporated by reference in its entirety for all purposes. In a similar manner, arrays could be constructed to test for a variety of sequence variations including deletions, repeats or base changes greater than one nucleotide. U.S. Pat. Nos. 5,593,839 and 5,856,101 (each of which is incorporated by reference for all purposes) describe methods of using computers to design arrays and lithographic masks.

The label used to detect the target sequences will be determined, in part, by the detection methods being applied. Thus, the labeling method and label used are selected in combination with the actual detecting systems being used. Once a particular label has been selected, appropriate labeling protocols will be applied, as described below for specific embodiments. Standard labeling protocols for nucleic acids are described, e.g., in Maniatis; Kambara, H. et al. (1988) BioTechnology 6:816–821; Smith, L. et al. (1985) Nuc. Acids Res. 13:2399–2412; for polypeptides, see, e.g., Allen G. (1989) Sequencing of Proteins and Peptides, Elsevier, N.Y., especially chapter 5, and Greenstein and Winitz (1961) Chemistry of the Amino Acids, Wiley and Sons, N.Y. Carbohydrate labeling is described, e.g., in Chaplin and Kennedy (1986) Carbohydrate Analysis: A Practical Approach, IRL Press, Oxford. Other techniques such as TdT end labeling may likewise be employed. Techniques for labeling protocols for use with SBE are described in, e.g. U.S. Provisional Patent Application 60/140,359 which is incorporated by reference above.

Generally, when using a DNA array a quickly and easily detectable signal is preferred. Fluorescent tagging of the target sequence is often preferred, but other suitable labels include heavy metal labels, magnetic probes, chromogenic labels (e.g., phosphorescent labels, dyes, and fluorophores) spectroscopic labels, enzyme linked labels, radioactive labels, and labeled binding proteins. Additional labels are described in U.S. Pat. Nos. 5,800,992 and 4,366,241, and published PCT Application WO 99/13319 which are incorporated herein by reference.

The hybridization conditions between probe and target should be selected such that the specific recognition interaction, i.e., hybridization, of the two molecules is both sufficiently specific and sufficiently stable. See, e.g., Hames and Higgins (1985) Nucleic Acid Hybridisation: A Practical Approach, IRL Press, Oxford. These conditions will be dependent both on the specific sequence and often on the guanine and cytosine (GC) content of the complementary hybrid strands. The conditions may often be selected to be universally equally stable independent of the specific sequences involved. This typically will make use of a reagent such as an alkylammonium buffer. See, Wood et al. (1985) "Base Composition-independent Hybridization in Tetramethylammonium Chloride: A Method for Oligonucleotide Screening of Highly Complex Gene Libraries," Proc. Natl. Acad. Sci. USA, 82:1585–1588; and Krupov et al. (1989) "An Oligonucleotide Hybridization Approach to DNA Sequencing," FEBS Letters, 256:118–122; each of which is hereby incorporated herein by reference. An alkylammonium buffer tends to minimize differences in hybridization rate and stability due to GC content. By virtue of the fact that sequences then hybridize with approximately equal affinity and stability, there is relatively little bias in strength or kinetics of binding for particular sequences. Temperature and salt conditions along with other buffer parameters should be selected such that the kinetics of renaturation should be essentially independent of the specific target subsequence or oligonucleotide probe involved. In order to ensure this, the hybridization reactions will usually be performed in a single incubation of all the substrate matrices together exposed to the identical same target probe solution under the same conditions. The hybridization conditions will usually be selected to be sufficiently specific such that the fidelity of base matching will be properly discriminated. Of course, control hybridizations should be included to determine the stringency and kinetics of hybridization. See for example, U.S. Pat. No. 5,871,928 which is hereby incorporated in its entirety for all purposes.

Another factor that can be adjusted to increase the ability of targets to hybridize to probes is the use of nucleic acid analogs of PNAs in the probes. They can be built into the probes to create a more uniform set of hybridization conditions across the entire array. See U.S. patent application Ser. No. 08/630,427 incorporated by reference above.

The detection methods used to determine where hybridization has taken place will typically depend upon the label selected. Thus, for a fluorescent label a fluorescent detection apparatus will typically be used. Pirrung et al. (1992) U.S. Pat. No. 5,143,854 and Ser. No. 07/624,120, now abandoned, (both of which are hereby incorporated by reference for all purposes) describe apparatus and mechanisms for scanning a substrate matrix using fluorescence detection, but a similar apparatus is adaptable for other optically detectable labels. See also, U.S. Pat. Nos. 5,578, 832, 5,834,758, and 5,837,832 each of which is incorporated by reference in its entirety for all purposes.

A variety of methods can be used to enhance detection of labeled targets bound to a probe attached to a solid support. In one embodiment, the protein MutS (from *E. coli*) or equivalent proteins such as yeast MSH1, MSH2, and MSH3; mouse Rep-3, and Streptococcus Hex-A, is used in conjunction with target hybridization to detect probe-target complex that contain mismatched base pairs. The protein, labeled directly or indirectly, can be added during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues. Signal amplification methods as described in U.S. patent application Ser. No. 09/276,774 may likewise be used.

Various methods of hybridization detection will be known to those of skill in the art. See for example, U.S. Pat. Nos. 5,578,832, 5,631,734, 5,744,305 and 5,800,992 each of which is hereby incorporated in its entirety for all purposes.

EXAMPLES

Example 1

Restriction Enzyme Digest/Sizing

The complexity of total genomic DNA from human and yeast was reproducibly reduced using a restriction enzyme digestion. For each species 0.5 ug genomic DNA was digested with 20 units of EcoRI in a total volume of 40 ul at 37° C. overnight (FIG. 2, Step 1). The enzyme was inactivated by incubation at 65° C. for 10 minutes.

The DNA solution was mixed with 10 ul 5×loading buffer and separated by gel electrophoresis on a 2% agarose gel. (FIG. 2, Step 2) The gel was visualized by ethidium bromide staining. Fragments of 250–350 bp were excised from the gel and purified using a QIAquick gel extraction kit (Qiagen). (FIG. 2, Step 3) Alternatively, fragments of the required size could have been isolated using HPLC.

Adaptor sequences containing PCR primer template sequences were then ligated to the purified fragments using 100U T4 ligase in 1×T4 DNA ligase buffer (New England Biolabs) at 16° C. overnight. The adaptor sequences were 5'-d(pAATTCGAACCCCTTCGGATC)-3' (SEQ ID NO: 3) and 5'-d(GATCCGAAGGGGTTCGAATT)-3' (SEQ ID NO: 4) (FIG. 2, Step 4) The ligase was then heat inactivated at 65° C. for 15 minutes.

The fragments were then subjected to PCR with one primer that corresponded to the PCR primer template sequence 5'-d(GATCCGAAGGGGTTCGAATT)-3' (SEQ ID NO: 5) (FIG. 2, Step 5). The PCR mixture contained approx. 1 ng ligated DNA fragments, 5 units AmpliTaq Gold polymerase (Perkins Elmer), 5 uM pimer, 200 uM dNTPs, 15 mM Tris-HCl (pH8.2), 50 mM KCl, 2.5 mM MgCl$_2$ in a final volume of 50 ul. PCR was performed in a Perkin-Elmer 9600 thermocycler using an initial 10 minute denaturation at 95° C., 35 cycles of a 1 minute denaturation at 94° C., annealing for 1 minute at 57° C. and extension at 72° C. for 2 minutes. This is followed by a final 5 minute extension cycle at 72° C.

The PCR products were then purified with QIAquick PCR Purification kit (Qiagen) according to the manufacturer's instructions and fragmented with DNase I.

The remaining fragments were then labeled with biotin-N6-ddATP as follows: In each tube, incubate 10 ug DNA with 0.3 unit DnaseI (Promega) at 37° C. for 30 minutes in a 45 ul mixture also containing 10 mM Tris-Actate (pH 7.5), 10 mM magnesium acetate and 50 mM potassium acetate. Stop the reaction by heating the sample to 95° C. for 15 minutes. Label the sample by adding 60 unit terminal transferase and 4 pmol biotin-N6-ddATP (Dupont NEN) followed by incubation at 37° C. for 90 minutes and a final heat inactivation at 95° C. for 15 minutes.

The labeled DNA was then hybridized to an array in a hybridization mixture containing 80 ug labeled DNA, 160 ug human COT-1 DNA (GIBCO), 3.5 M tetramethylamonium cloride, 10 mM MES (pH 6.5), 0.01% Triton-100, 20 ug herring sperm DNA, 100 ug bovine serum albumin and 200 pM control oligomer at 44° C. for 40 hours on a rotisserie at 40 rpm. The arrays were then washed with 0.1 M MaCl in 10 mM MES at 44° C. for 30 minutes on a rotisserie at 40 rpm. The hybridized arrays were then stained with a staining solution [10 mM MES (ph 6.5), 1 M NaCl, 10 ug/ml steptaviden R-phycoerythrin, 0.5 mg/ml acetylated BSA, 0.01% Triton-100] at 40° C. for 15 minutes. The arrays were then washed with 6×SSPET [0.9 M NaCl, 60 mM NaH2PO4 (pH 7.4), 6 mM EDTA, 0.005% Triton-100] on a GeneChip® Fluidics Station (Affymetrix, Inc., Santa Clara, Calif.) 10 times at 22° C. The arrays were then anti-streptavidin antibody stained at 40° C. for 30 minutes with antibody solution [10 mM MES (pH 6.5), 1 M NaCl, 10 ug/ml streptavidin R-phycoerythrin, 0.5 mg/ml actylated BSA, 0.01% Triton-100]. The arrays were then restained with staining solution for 15 minutes followed by 6×SSPET washing as above. The arrays were then scanned with a confocal scanner at 560 nm. The hybridization patterns were then screened for SNP detection with a computer program as described in D. G. Wang et al Science 280, 1077–1082, 1998. The results of the hybridization can be seen in FIGS. 8A and 8B.

Example 2

Digestion with a Type IIs Endonuclease and Selective Ligation

Complexity was reproducibly reduced after digestion with a type IIs endonuclease and selective ligation to an adaptor sequence. 2 ug of genomic DNA was digested with Bbv I at 37° C. overnight. (FIG. 3, Step 1) The enzyme was heat inactivated at 65° C. for 15 minutes.

Adaptors containing PCR primer template sequences were ligated in a 50 ul mixture of 400 ng digested genomic DNA, 10 pmol adaptor and 40 unit T4 ligase in a 1×T4 ligase buffer. (FIG. 3, Step 2) The adaptor sequences were as follows: 5'-d(pATNNGATCCGAAGGGTTCGAATTC)-3' (SEQ ID NO: 6) and 5'(GAATTCGAACCCCTTCGGATC)-3' (SEQ ED NO: 7). The ligation was conducted at 16° C. overnight. The ligase was inactivated by incubation at 65° C. for 15 minutes.

The fragments were then subjected to PCR with one primer that corresponded to the PCR primer template sequence: 5'-(GAATTCGAACCCCTTCGGATC)-3' (SEQ ID NO: 8) in a 50 ul reaction containing 20 ng ligated DNA, 1 unit AmpliTaq Gold polymerase (Perkins Elmer), 3 uM prira, 200 uM dNTPs. 15 mM Tris-HCI (pH8.0), 50 mM KCl, 2.5 mM MgCl$_2$. PCR was performed in a Perkin-Elmer 9600 thermocycler using an initial 10 minute denaturation at 95° C., 35 cycles of a 0.5 minute denaturation at 94° C., annealing for 0.5 minute at 57° C. and extension at 72° C. for 2 minutes. This is followed by a final 5 minute extension cycle at 72° C.

Example 3
Double Digestion and Selective PCR

Human genomic DNA was digested in a 40 ul reaction at 37° C. for 1 hour. The reaction mixture contained 0.5 ug human genomic DNA, 0.5 mM DTT, 5 unit EcoRI (New England Biolabs), 5 units Sau3AI (New England Biolabs), 0.5 ng/ul BSA, 10 mM Tris-Acetate (pH 7.5), 10 mM magnesium acetate and 50 mM potassium acetate. The enzymes were inactivated at 65° C. for 15 minutes.

The restriction fragments were then ligated to adaptor sequences. The ligation mixture contained: 5 pmol Eco RI adaptor [5'-d(pAATTCGAACCCCTTCGGATC)-3' (SEQ ID NO; 9) and 5'-d(GATCCGAAGGGGTTCG)-3' (SEQ ID NO: 10)], 50 pmol Sau3A I adaptor [5'-d (pGATCGCCCTATAGTGAGTCGTATTACAGTGGAC CATCGAGGGTCA)-3' (SEQ ID NO: 11)], 5 mM DTT, 0.5 ng/ul BSA, 100 unit T4 DNA ligase, 1 mM ATP, 10 mM Tris-Acetate (pH 7.5), 10 mM magnesium acetate and 50 mM potassium acetate]. The ligation mixture was incubated with the restriction fragments at 37° C. for 3 hours. The ligase was inactivated at 65° C. for 20 minutes.

The ligated DNA target was then amplified by PCR The PCR mixture contained 12.5 ng ligated DNA, 1 unit Ampli-Taq Gold polymerase (Perkns Elmer), 0.272 mM EcoRI selective primer (5'-AAGGGGTTCGGAATTCCC-3'; (SEQ ID NO: 12) CC as the selective bases), 0.272 uM Sau3AI selective primer (5'-TCACTATAGGGCGATCTG-3'; (SEQ ID NO: 13) TG as the selective bases), 200 uM dNTPs, 15 mM Tris-HCl (pH 8,0), 50 mM KCl, 2.5 mM MgCl$_2$ in a final volume of 50 ul. PCR was performed in a Perkin-Elmer 9600 thermocycler using an initial 10 minute denaturation at 95° C., 35 cycles of a 1 minute denaturation at 94° C., annealing for 1 minute at 56° C. and extension at 72 for 2 minutes. This is followed by a final 5 minute extension at 72° C. annealing for 1 minute at 56° C. and extension at 72 for 2 minutes. This is followed by a final 5 minute extension at 72° C.

Example 4
Arbitrarily Primed PCR

PCR primers were designed with the Operon Oligo Toolkit described in the specification above.

Human genomic DNA was amplified in a 100 ul reaction containing 100 ng genomic DNA, 1.25 units AmpliTaq Gold polymerase (Perkin Elmer), 10 uM arbitrary primer, 200 mM dNTPs, 10 mM tris-HCl (pH 8.3), 50 mM KCl and 2.5 mM MgCl$_2$.

PCR was performed in a Perkin-Elmer 9600 thermocycler using an initial 10 minute denaturation at 95° C., 35 cycles of a 1 minute denaturation at 94° C., annealing for 1 minute at 56° C. and extension at 72 for 2 minutes. This is followed by a final 7 minute extension at 72° C.

The PCR product was then purified, fragmented, labeled and hybridized as described in the examples above.

Example 5
SNP Discovery—Generally

As an example, the present invention may be directed to a method for simplifying the detection of or comparing the presence of absence of SNPS among individuals, populations, species or between different species. This invention allows for a quick and cost-effective method of comparing polymorphism data between multiple individuals. First, a reduced representation of a nucleic acid sample is produced in a repeatable and highly reproducible manner from multiple individuals, using any of the above described techniques alone or in combination. Then, the data generated by hybridizing the DNA samples collected from multiple individuals to identical arrays in order to detect for the presence or absence of a number of sequence variants is compared. Arrays are designed to detect specific SNPS or simply to detect the presence of a region known to frequently contain SNPS. In the latter case, other techniques such as sequencing could be employed to identify the SNP.

SNP Discovery—Method 1

Typically, the detection of SNPs has been made using at least one procedure in which the nucleic acid sequence that may contain the SNP is amplified using PCR primers. This use can create an expense if many SNPs are to be evaluated or tested and it adds significantly more time to the experiment for primer design and selection and testing. The following example eliminates the need for the specific PCR amplification step or steps. First, using the methods provided in example 1 above, a restriction enzyme or enzymes is used to cut genomic DNA at a large number of sites and a size range of restriction fragments is selected for assay. An electronic database, such as GenBank is queried to determine which sequences would be cut with the specific restriction enzyme(s) that were selected above. The sequences of the resulting fragments are then used to design DNA arrays which will screen the regions for the SNPs or other variants. The selected fragments are then subjected to further fragmentation and hybridized to the array for analysis.

SNP Discovery—Method 2

Alternatively, the method provided in example 2 above may be employed, type IIS restriction enzymes cut genomic DNA from each individual and adaptor sequences are designed to ligate to specific fragments as desired. Adaptor sequences may include both random and specific nucleotide ends as required to produce the desired result. If desired, amplification primers may be designed to hybridize to the adaptor sequences, allowing for amplification of only the fragments of interest. An electronic database and computer modeling system may be used to aid in the selection of appropriate experimental conditions and to design the appropriate arrays. The fragments are then hybridized to the array for analysis.

SNP Discovery—Method 3

As another alternative, MutS Protein were used to isolate DNA containing SNPS for analysis on an array. 3 ugs of DNA was fragmented with Eco RI (alternatively a Dnase I could have been used.) At this point an equal amount of control DNA was added (this step is optional).

0.5 ug of the fragments were denatured at 95° C. for 10 minutes and gradually cooled to 65° C. over a 60 minute period. The fragments were then incubated at 65° C. for 30 minutes and the temperature was ramped down to 25° C. over a 60 minute period. 1.5 ug MutS protein (Epicentre) was then added and allowed to incubate at room temperature for 15 minutes to allow for binding. (FIG. 7, Step 1)

The bound fragments were then digested with 20 units T7 polymerase (New England Biolabs) at 30° C. for 30 minutes. (FIG. 7, Step 2) The T7 polymerase was inactivated by incubation at 65° C. for 10 minutes.

Single stranded DNA was trimmed with 100 units of nuclease S1 (Boehringer-Mannheim) at 16° C. for 15 minutes. (FIG. 7, Step 3) The enzymes inactivated by adding 50 nmol EDTA and incubation at 65° C. for 15 minutes.

Adaptor sequences containing PCR primer templates were then ligated to the DNA sequences in a 10 ul ligation mixture: 1 ul DNA solution, 4 ul dH2O, 1 ul 10×T4 DNA ligase buffer, 3 ul 10 mM adaptor [5'-d(GATCCGAAGGGGTTCGAATT)-3' (SEQ ID NO: 14) and 5'-d(pGAATTCGAACCCCTTCGGATC-3') (SEQ ID NO: 15) and 1 ul 400 U/ul T4 DNA ligase] and incubated at 16° C. overnight and then inactivated at 65° C. for 15 minutes. (FIG. 7, Step 4).

The sequences were amplified in a 25 ul reaction containing 0.25 pmol template DNA, 0.125 units AmpliTaq Gold polymerase (Perkin Elmer), 3 uM primer, [5'-d(GAATCCGAAGGGGTTCGAATT)-3' (SEQ ID NO: 16)], 200 uM dNTPs, 15 mM tris-HCl (pH 8.0), 50 mM KCl and 1.5 mM MgCl$_2$.

PCR was performed in a MJ Research Tetrad thermocycler using an initial 10 minute denaturation at 95° C., 35 cycles of a 0.5 minute denaturation at 94° C., annealing for 0.5 minute at 57° C. and extension at 72° C. This was followed by a final 5 minute extension at 72° C.

The sequences were then labeled and hybridized to an array as described above.

SNP Discovery—Method 4

As another alternative, oligonucleotides attached to magnetic beads may be used for allele specific SNP enrichment and genotyping. Synthesized biotin-tagged oligonucleotides containing sequences complementary to the regions of desired SNPs were mixed with target DNA in a 1000:1 ratio. (Alternatively, a 10:1, 20:1, 50:1, 250:1 or any other ratio could have been chosen.)

The sample was then denatured at 95° C. for 10 minutes and allowed to reanneal by slowly cooling to room temperature.

The sample was then bound to streptavadin-magnetic beads (Promega) by mixing the sample and the beads and incubation at room temperature for 10 minutes. The beads were then washed with 1×MES with 1M Sodium Chloride (NaCl) three times. The beads were then resuspended in 50 ul 1×mung bean nuclease buffer and mixed with 1 unit of mung bean nuclease. The beads were then incubated at 30° C. for 15 minutes. The mung bean nuclease was then inactivated by adding 1% SDS. The beads were then washed with 1×MES with 1M NaCl three times.

The beads were then resuspended in ligation mixture containing T4 ligase in 1×T4 ligase buffer and 200 fold excess adaptor I sequence [5'-d(ATTAACCCTCACTAAAGCTGGAG)-3' (SEQ ID NO: 17) and 5'-d(pCTCCAGCTTTAGTGAGGGTTAAT)-3' (SEQ ID NO: 18) BpmI recognition sites are highlighted in boldface] at 16° C. overnight. The ligase was then inactivated by incubation at 65° C. for 10 minutes.

The beads were then washed with 1X MES with 1M NaCl three times and then resuspended in 50 ul 1×Bpm I restriction buffer. BPM I was then added and the beads were incubated at 37° C. for 1 hr. The enzyme was inactivated by incubation at 65° C. for 10 minutes and the supernatant solution with the sequences containing the desired SNPs was collected.

A second set of adaptor sequences containing PCR template sequences [5'-d(pCTATAGTGAGTCGTATT-3') (SEQ ID NO: 19) and (5'-AATACGACTCACTATAGNN-3') (SEQ ID NO: 20)] and ligase were then added to the superatant solution and incubated at 16° C. overnight. The ligase was then heat inactivated at 65° C. for 10 minutes.

The samples were then amplified with PCR using T3 (5'-ATTAACCCTCACTAAAG-3') (SEQ ID NO: 21) and T7 5'-d(TAATACGACTCACTATAGGG)-3' (SEQ ID NO: 22) sequencing primers (Operon) in a 50 ml reaction containing 10$^6$ copies of each target DNA, 1 unit AmpliTaq Gold polymerase (Perkin Elmer), 2 uM each primer, 200 uM dNTPs, 15 mM tris-HCl (pH 8.0), 50 mM KCl and 2.5 mM MgCl$_2$.

PCR was performed in a MJ Research Tetrad Thermocycler using an initial 10 minute denaturation at 95° C., 45 cycles of a 0.5 minute denaturation at 94° C., annealing for 0.5 minute at 52° C. and extension at 72° C. for 1 minute. This was followed by a final 5 minute extension at 72° C. The fragments were then labeled and hybridized to an array.

Methods of Use

The present methods of sample preparation and analysis are appropriate for a wide variety of applications. Any analysis of genomic DNA may be benefitted by a reproducible method of complexity management.

As a preferred embodiment, the present procedure can be used for SNP discovery and to genotype individuals. For example, any of the procedures described above, alone or in combination, could be used to isolate the SNPs present in one or more specific regions of genomic DNA. Arrays could then be designed and manufactured on a large scale basis to interrogate only those fragments containing the regions of interest. Thereafter, a sample from one or more individuals would be obtained and prepared using the same techniques which were used to design the array. Each sample can then be hybridized to a pre-designed array and the hybridization pattern can be analyzed to determine the genotype of each individual or a population of individuals as a whole. Methods of use for polymorphisms can be found in, for example, co-pending U.S. application Ser. No. 08/813,159. Some methods of use are briefly discussed below.

Correlation of Polymorphisms with Phenotypic Traits

Some polymorphisms occur within a protein coding sequence and contribute to phenotype by affecting protein structure. The effect may be neutral, beneficial or detrimental, or both beneficial and detrimental, depending on the circumstances. For example, a heterozygous sickle cell mutation (which involves a single nucleotide polymorphism) confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but hitherto unmapped genetic components (e.g., agammaglobulimenia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagic telangiectasia, familial colonic polyposis, Ehlers-Danlos syndrome, osteogenesis imperfecta, and acute intermittent porphyria). Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a chi-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal. (See, Beitz et al., U.S. Pat. No. 5,292,639).

Genetic Mapping of Phenotypic Traits

Linkage analysis is useful for mapping a genetic locus associated with a phenotypic trait to a chromosomal position, and thereby cloning gene(s) responsible for the trait. See Lander et al., *Proc. Natl. Acad. Sci. (USA)* 83, 7353–7357 (1986); Lander et al., *Proc. Natl. Acad. Sci. (USA)* 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J Australia* 159, 170–174 (1993); Collins, *Nature Genetics* 1, 3–6 (1992) (each of which is incorporated by reference in its entirety for all purposes).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Disequilibrium Mapping of the Entire Genome

Linkage disequilibrium or allelic association is the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Marker Assisted Breeding

Genetic markers can decipher the genomes in animals and crop plants. Genetic markers can aid a breeder in the understanding, selecting and managing of the genetic complexity of an agronomic or desirable trait. The agriculture world, for example, has a great deal of incentive to try to produce food with a rising number of desirable traits (high yield, disease resistance, taste, smell, color, texture, etc.) as consumer demand and expectations increase. However, many traits, even when the molecular mechanisms are known, are too difficult or costly to monitor during production. Readibly detectable polymorphisms which are in close physical proximity to the desired genes can be used as a proxy to determine whether the desired trait is present or not in a particular organism. This provides for an efficient screening tool which can accelerate the selective breeding process.

Pharmacogenomics

Genetic information can provide a powerful tool for doctors to determine what course of medicine is best for a particular patient. A recent Science paper entitled "Molecular Classification of Cancer: Class Discovery and Class Prediction by Gene Expression Monitoring," (to be published Oct. 15, 1999 hereby incorporated by reference in its entirety for all purposes) discusses the use of genetic information discovered through the use of arrays to determine the specific type of cancer a particular patient has. The paper goes on to discuss the ways in which particular treatment options can then be tailored for each patient's particular type of cancer. Similar uses of genetic information for treatment plans have been disclosed for patients with HIV. (See U.S. patent application Ser. No. 5,861,242).

The pharmaceutical industry is likewise interested in the area of pharmacogenomics. Every year pharmaceutical companies suffer large losses from drugs which fail clinical trials for one reason or another. Some of the most difficult are those drugs which, while being highly effective for a large percentage of the population, prove dangerous or even lethal for a very small percentage of the population. Pharmacogenomics can be used to correlate a specific genotype with specific responses to a drug. The basic idea is to get the right drug to the right patient. If pharmaceutical companies (and later, physicians) can accurately remove from the potential recipient pool those patients who would suffer adverse responses to a particular drug, many research efforts which are currently being dropped by pharmaceutical companies could be resurrected saving hundreds of thousands of dollars for the companies and providing many currently unavailable medications to patients.

Similarly, some medications may be highly effective for only a very small percentage of the population while proving only slightly effective or even ineffective to a large percentage of patients. Pharmacogenomics allows pharmaceutical companies to predict which patients would be the ideal candidates for a particular drug, thereby dramatically reducing failure rates and providing greater incentive to companies to continue to conduct research into those drugs.

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

Paternity Testing/Determination of Relatedness

The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child. Of course, the present invention can be expanded to the use of this procedure to determine if one individual is related to another. Even more broadly, the present invention can be employed to determine how related one individual is to another, for example, between races or species.

Conclusion

From the foregoing it can be seen that the advantage of the present invention is that it provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to isolation of desired fragments and hybridization to an appropriate array, the above invention provides for faster, more efficient and less expensive methods of complex nucleic acid analysis.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of analyzing a first nucleic acid sample comprising:
   providing said first nucleic acid sample;
   obtaining a second nucleic acid sample by:
   (a) fragmenting said first nucleic acid sample to produce fragments, ligating adaptor sequences to said fragments, amplifying at least some of said fragments, and isolating said amplified fragments; or
   (b) fragmenting said first nucleic acid sample to produce fragments, denaturing said fragments, allowing at least some of said fragments to reanneal to form double stranded DNA sequences and removing said double stranded DNA sequences thus isolating said single stranded fragments; or
   (c) amplifying said first nucleic acid sample by arbitrarily primed PCR to produce an amplification product and isolating said amplification product; or
   (d) fragmenting said first nucleic acid sample to produce fragments, hybridizing said fragments to an oligonucleotide probe bound to a solid support, and isolating said hybridized fragments; or
   (e) fragmenting said first nucleic acid sample to produce fragments, binding said fragments to a mismatch binding protein, and isolating said bound fragments;
   providing a nucleic acid array;
   hybridizing said second nucleic acid sample to said array; and analyzing a hybridization pattern resulting from said hybridization.

2. The method of claim 1 wherein said second nucleic acid sample comprises at least 0.5% of said first nucleic acid sample.

3. The method of claim 1 wherein said second nucleic acid sample comprises at least 3% of said first nucleic acid sample.

4. The method of claim 1 wherein said second nucleic acid sample comprises at least 12% of said first nucleic acid sample.

5. The method of claim 1 wherein said second nucleic acid sample comprises at least 50% of said first nucleic acid sample.

6. The method of claim 1 wherein said first nucleic acid sample is DNA.

7. The method of claim 1 wherein said first nucleic acid sample is genomic DNA.

8. The method of claim 1 wherein said first nucleic acid sample is cDNA derived from RNA or mRNA.

9. The method of claim 1 wherein steps (b), (d) and (e) further comprise the step of amplifying the isolated fragments.

10. The method of claim 9 wherein said step of amplifying is performed by a polymerase chain reaction (PCR).

11. The method of claim 1 wherein the entire method is performed in a single reaction vessel.

12. The method of claim 1 wherein said step of fragmenting the first nucleic acid sample comprises digestion with at least one restriction enzyme.

13. The method of claim 1 wherein said step of fragmenting the first nucleic acid sample comprises digestion with a type IIs endonuclease.

14. The method of claim 1 wherein said adaptor sequences comprise PCR primer template sequences.

15. The method of claim 1 wherein said adaptor sequences comprise tag sequences.

16. The method of claim 1 wherein said solid support is a magnetic bead.

17. The method of claim 1 wherein said mismatch binding protein is bound to a magnetic bead.

18. The method of claim 1 wherein said method for analyzing a first nucleic acid sample comprises determining whether the first nucleic acid sample contains sequence variations.

19. The method of claim 18 wherein said sequence variations are single nucleotide polymorphisms (SNPs).

20. The method of claim 1 wherein the nucleic acid array is designed to query DNA fragments which have been produced by the identical procedures used to obtain said second nucleic acid sample.

21. The method of claim 20 wherein the sequences contained in said second nucleic acid sample are predetermined.

22. The method of claim 20 wherein said sequences contained in said second nucleic acid sample are first determined by a computer system.

23. The method of claim 19 wherein said second nucleic acid sample is obtainable by:
   binding oligonucleotide probes containing a desired SNP sequence to magnetic beads to form probe-bead complexes;
   hybridizing said probe-bead complexes to said first nucleic acid sample;
   exposing said first nucleic acid sample to a single strand DNA nuclease to remove single stranded DNA thereby obtaining only DNA duplexes;
   ligating a double stranded adaptor sequence comprising a restriction enzyme site to said DNA duplexes;
   digesting said DNA duplexes with a restriction enzyme to release the magnetic bead; and
   isolating the duplexes.

24. The method of claim 23 wherein said restriction enzyme is a Class IIs endonuclease.

25. A method of screening for DNA sequence variations in an individual comprising:
   providing a first nucleic acid sample from said individual;
   obtaining a second nucleic acid sample by:
   (a) fragmenting said first nucleic acid sample to produce fragments, ligating adaptor sequences to said fragments, amplifying at least some of said fragments, and isolating said amplified fragments; or
   (b) fragmenting said first nucleic acid sample to produce fragments, denaturing said fragments, allowing some of said fragments to reanneal to form double stranded DNA sequences and removing said double stranded DNA sequences thus isolating said single stranded fragments; or
   (c) amplifying said first nucleic acid sample by arbitrarily primed PCR to produce an amplification product and isolating said amplification product; or
   (d) fragmenting said first nucleic acid sample to produce fragments, hybridizing said fragments to an oligonucleotide probe bound to a solid support, and isolating said hybridized fragments; or
   (e) fragmenting said first nucleic acid sample to produce fragments, binding said fragments to a mismatch binding protein, and isolating said bound fragments;
   providing a nucleic acid array wherein said array comprises probes designed to interrogate for DNA sequence variations;
   hybridizing said second nucleic acid sample to said array;
   generating a hybridization pattern resulting from said hybridization; and determining the presence or absence of DNA sequence variations in the individual based upon an analysis of the hybridization pattern.

26. The method of claim 25 wherein said sequence variation is a single nucleotide polymorphism (SNP).

27. The method of claim 26 wherein said SNP is associated with a disease.

28. The method of claim 26 wherein said SNP is associated with the efficacy of a drug.

29. A method of screening for DNA sequence variations in a population of individuals comprising:

providing a first nucleic acid sample from each of said individuals;

providing a second nucleic acid sample by:
  (a) fragmenting said first nucleic acid sample to produce fragments, ligating adaptor sequences to said fragments, amplifying at least some of said fragments, and isolating said amplified fragments; or
  (b) fragmenting said first nucleic acid sample to produce fragments, denaturing said fragments, allowing some of said fragments to reanneal to form double stranded DNA sequences and removing said double stranded DNA sequences thus isolating said single stranded fragments; or
  (c) amplifying said first nucleic acid sample by arbitrarily primed PCR to produce an amplification product and isolating said amplification product; or
  (d) fragmenting said first nucleic acid sample to produce fragments, hybridizing said fragments to an oligonucleotide probe bound to a solid support, and isolating said hybridized fragments; or
  (e) fragmenting said first nucleic acid sample to produce fragments, binding said fragments to a mismatch binding protein, and isolating said bound fragments;

providing a plurality of identical nucleic acid arrays wherein said arrays comprise probes which are designed to interrogate for DNA sequence variations;

hybridizing each of said second nucleic acid samples to one of said plurality of identical arrays; and generating a plurality of hybridization patterns resulting from said hybridizations; and analyzing the hybridization patterns to determine the presence or absence of sequence variation in the population of individuals.

30. The method of claim 29 wherein said sequence variation is a single nucleotide polymorphism.

* * * * *

SEQUENCE LISTING

```
<160> NUMBER OF SEQ ID NOS: 22

<210> SEQ ID NO 1
<211> LENGTH: 11
<212> TYPE: DNA
<213> ORGANISM: Artificial Sequence
<220> FEATURE:
<223> OTHER INFORMATION: Endonuclease Ear I cut site
<221> NAME/KEY: misc_feature
<222> LOCATION: (7)..(11)
<223> OTHER INFORMATION: n=any nucleotide

<400> SEQUENCE: 1
ctcttcnnnn n                                                            11

<210> SEQ ID NO 2
<211> LENGTH: 11
<212> TYPE: DNA
<213> ORGANISM: Artificial Sequence
<220> FEATURE:
<223> OTHER INFORMATION: Endonuclease EarI CUT SITE
<221> NAME/KEY: misc_feature
<222> LOCATION: (7)..(11)
<223> OTHER INFORMATION: n=any nucleotide

<400> SEQUENCE: 2
gagaagnnnn n                                                            11

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
aattcgaacc ccttcggatc                                                   20
```

```
<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
gaccgaaggg gttcgaatt                                                   19

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
gatccgaagg ggttcgaatt                                                  20

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (3)..(4)
<223> OTHER INFORMATION: n=any nucleotide

<400> SEQUENCE: 6
atnngatccg aagggttcga attc                                             24

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 7
gaattcgaac cccttcggat c                                                21

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
gaattcgaac cccttcggat c                                                21

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
aattcgaacc ccttcggatc                                                  20

<210> SEQ ID NO 10
<211> LENGTH: 16
```

```
<212> TYPE: DNA
<213> ORGANISM: Artificial Sequence
<220> FEATURE:
<223> OTHER INFORMATION: synthetic oligonucleotide

<400> SEQUENCE: 10
gatccgaagg ggttgg                                               16

<210> SEQ ID NO 11
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 11
gatcgcccta tagtgagtcg tattacagtg gaccatcgag ggtca               45

<210> SEQ ID NO 12
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 12 aagggttcg gaattccc                                              18

<210> SEQ ID NO 13
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 13
tcactatagg gcgatctg                                             18

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
gatccgaagg ggttcgaatt                                           20

<210> SEQ ID NO 15
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 15
gaattcgaac cccttcggat c                                         21

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
```
gatccgaagg ggttcgaatt                                                      20

<210> SEQ ID NO 17
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 17 attaccctc actaaagctg gag                                                   23

<210> SEQ ID NO 18
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 18
ctccagcttt agtgagggtt aat                                                  23

<210> SEQ ID NO 19
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 19
ctatagtgag tcgtatt                                                         17

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (18)..(19)
<223> OTHER INFORMATION: n=any nucleotide

<400> SEQUENCE: 20
aatacgactc actatagnn                                                       19

<210> SEQ ID NO 21
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 21 attaccctc actaaag                                                          17

<210> SEQ ID NO 22
<211> LENGTH: 20
<212> TYPE: DNA
<213> ORGANISM: Artificial Sequence
<220> FEATURE:
<223> OTHER INFORMATION: synthetic primer

<400> SEQUENCE: 22
taatacgact cactataggg                                                      20